United States Patent [19]

Brown et al.

[11] 4,238,606
[45] Dec. 9, 1980

[54] TRICYCLIC MONO-CHROMONE-2-CARBOXYLIC ACIDS

[75] Inventors: Roger C. Brown, Loughborough; Richard Hazard, Cropston; John Mann, Long Whatton, all of England

[73] Assignee: Fisons Limited, London, England

[21] Appl. No.: 35,739

[22] Filed: May 3, 1979

Related U.S. Application Data

[60] Division of Ser. No. 869,654, Jan. 16, 1978, Pat. No. 4,159,273, which is a continuation of Ser. No. 632,217, Nov. 17, 1975, abandoned.

[30] Foreign Application Priority Data

| Nov. 30, 1974 | [GB] | United Kingdom | 51994/74 |
| Dec. 12, 1974 | [GB] | United Kingdom | 53704/74 |
| May 16, 1975 | [GB] | United Kingdom | 21043/75 |
| May 16, 1975 | [GB] | United Kingdom | 21044/75 |

[51] Int. Cl.³ .......................................... C07D 311/22
[52] U.S. Cl. ............................... 542/441; 260/345.2
[58] Field of Search ................... 260/345.2; 542/441

[56] References Cited

U.S. PATENT DOCUMENTS

| 3,291,811 | 12/1966 | Wragg | 260/345.2 |
| 3,322,795 | 5/1967 | Ellis et al. | 260/345.2 |
| 3,484,445 | 12/1969 | Lee et al. | 260/345.2 |
| 3,629,290 | 12/1971 | Cairns et al. | 260/345.2 |
| 3,860,617 | 1/1975 | Cairns et al. | 260/345.2 |

FOREIGN PATENT DOCUMENTS

| 1481033 | 5/1967 | France | 260/345.2 |
| 1024645 | 3/1966 | United Kingdom | 260/345.2 |
| 1029213 | 5/1966 | United Kingdom | 260/345.2 |
| 1049289 | 11/1966 | United Kingdom | 260/345.2 |
| 1116562 | 6/1968 | United Kingdom | 260/345.2 |
| 1291864 | 10/1972 | United Kingdom | 260/345.2 |

*Primary Examiner*—Nicky Chan
*Attorney, Agent, or Firm*—Merriam, Marshall & Bicknell

[57] ABSTRACT

There are described compounds of formula I,

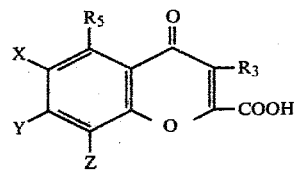

in which
$R_3$ represents hydrogen, or alkyl C 1 to 6,
$R_5$ represents hydrogen, hydroxy, alkoxy C 1 to 6, alkanoyloxy C 2 to 6, alkenyloxy C 2 to 6, nitro, $-NR_1R_2$, halogen, alkyl C 1 to 6, hydroxy-alkyl C 1 to 6, or hydroxy-alkoxy C 1 to 6,
an adjacent pair of X, Y and Z form a $-(CH_2)_4-$, $-CH=CH-CH=CH-$ or $-O(CH_2)_3-$ chain, each of the chains optionally being substituted by one or two C 1 to 6 alkyl groups, and the remaining substituent X or Z represents alkenyl C 2 to 6 optionally substituted by phenyl; halogen; or alkyl C 1 to 9 optionally substituted by one or more of the groups hydroxy, halogen, carbonyl oxygen, phenyl, or alkoxy C 1 to 6,
or, when an adjacent pair of X, Y and Z form a chain substituted by one or two C 1 to 6 alkyl groups, the remaining substituent X or Z may be hydrogen, and
$R_1$ and $R_2$, which may be the same or different, are each hydrogen or alkyl C 1 to 6,
and pharmaceutically acceptable derivatives thereof.

Processes for making the compounds and pharmaceutical, e.g. anti-allergic, compositions containing the compounds are also described.

9 Claims, No Drawings

TRICYCLIC MONO-CHROMONE-2-CARBOXYLIC ACIDS

This is a division of application Ser. No. 869,654, filed Jan. 16, 1978, now U.S. Pat. No. 4,159,273, which application is a continuation of application Ser. No. 632,217, filed Nov. 17, 1975, now abandoned.

This invention relates to new compounds, methods for their preparation and compositions containing them.

A large number of monochromone-2-carboxylic acids, monochromone-2-(5-1H)-tetrazoles, and benzodipyran-2-carboxylic acids have, in the past, been suggested as of possible utility in the treatment of conditions involving antibody/antigen reactions, e.g. allergic asthma. (See for Example British Patent Specifications Nos. 1,024,645; 1,032,362; 1,049,289; 1,093,673; 1,223,690; 1,116,562; 1,147,976; 1,291,864; 1,389,227; 1,321,879, 1,368,243; and 1,362,782 and French Patent Specification No. 1,481,033. In particular British Patent Specifications Nos. 1,029,213 and 1,230,087 are worthy of note. A number of these known compounds have been found to have activity in one or more of the various pharmacological tests used in this area of research, but have failed to be sufficiently well absorbed, or have been found to have other properties which are either unsatisfactory or inadequate, when administered oesophageally. A number of these monochromone compounds have also proved to have disadvantages when administered by inhalation, e.g. they are irritant or do not have adequate duration of action. In 1965 the bischromone compound di-sodium cromoglycate (British Patent Specification No. 1,144,905) was discovered and has subsequently been widely used for the inhalation therapy of allergic asthma. However inhalation therapy has, in certain instances, considerable disadvantages, e.g. in the use of complex devices for administration of the compound and the difficulty sometimes experienced by asthmatic subjects in inhaling powders. We have now found that a small and selected group of monochromone compounds are more readily absorbed when administered orally and/or possess other more advantageous properties, than structurally closely related known compounds.

According to our invention we provide compounds of formula I, in which $R_3$ represents hydrogen, or alkyl C 1 to 6, $R_5$ represents hydrogen, hydroxy, alkoxy C 1 to 6, alkanoyloxy C 2 to 6, alkenyloxy C 2 to 6, nitro, $-NR_1R_2$, halogen, alkyl C 1 to 6, hydroxy-alkyl C 1 to 6, or hydroxy-alkoxy C 1 to 6, an adjacent pair of X, Y and Z form a $-(CH_2)_4-$, $-CH=CH-CH=CH-$ or $-O(CH_2)_3-$ chain, each of the chains optionally being substituted by one or two C 1 to 6 alkyl groups, and the remaining substituent X or Z represents alkenyl C 2 to 6 optionally substituted by phenyl; halogen; or alkyl C 1 to 9 optionally substituted by one or more of the groups hydroxy, halogen, carbonyl oxygen, phenyl, or alkoxy C 1 to 6, or, when an adjacent pair of X, Y and Z form a chain substituted by one or two C 1 to 6 alkyl groups, the remaining substituent X or Z may be hydrogen, and $R_1$ and $R_2$, which may be the same or different, are each hydrogen or alkyl C 1 to 6, and pharmaceutically acceptable derivatives thereof.

According to our invention we also provide a process for the production of a compound of formula I, or a pharmaceutically acceptable derivative thereof, which comprises, (a) cyclising a compound of formula II, in which $R_5$, X, Y and Z are as defined above, $A^1$ and $A^2$ represent the pairs of groups (i) $-COCHR_3COCOR''$ and $-OM$ or a halogen atom, or (ii) $-H$ and $-O-C(COR'')=CR_3-COR''$ $R_3$ is as defined above, $R''$ represents $-OM$, or a group which is hydrolysable thereto, and M represents hydrogen or an alkali metal, and if necessary or desired hydrolysing the group $-COR''$, to a group $-COOM$, (b) selectively hydrolysing or oxidising a compound of formula III, in which $R_3$, $R_5$, X, Y and Z are as defined above, and D is a group which is hydrolysable or oxidisable to a $-COOM$ group, (c) selectively removing the groups A and B from a compound of formula IV, or an ester thereof, in which $R_3$, $R_5$, X, Y and Z are as defined above, and A and B are both hydrogen or one of A and B is hydrogen and the other is halogen or hydroxy, (d) production of a compound of formula I in which $R_3$, $R_5$, X, Y and Z are as defined above, with the proviso that at least one of the substituents $R_3$, $R_5$, X, Y and Z is selected from the following significances:

$R_3$ = alkyl C 1 to 6;
$R_5$ = alkoxy C 1 to 6 or alkyl C 1 to 6;
X or Z = alkyl C 1 to 9, or phenyl-alkyl in which the alkyl group contains from 1 to 6 carbon atoms;
an adjacent pair of X, Y and Z form a chain substituted by one or two alkyl C 1 to 6 groups;
by selective reduction of a corresponding compound of formula XX,

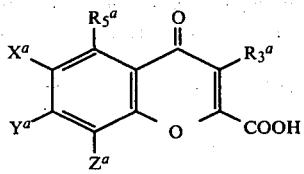

XX or an ester thereof, in which
$R_3{}^a$, $R_5{}^a$, $X^a$, $Y^a$ and $Z^a$ have the same significances as $R_3$, $R_5$, X, Y and Z above, save that at least one of $R_3{}^a$, $R_5{}^a$, $X^a$, $Y^a$ and $Z^a$ is selected from the following significances:
$R_3{}^a$ = a group reducible to alkyl C 1 to 6;
$R_5{}^a$ = a group reducible to alkoxy C 1 to 6 or to alkyl C 1 to 6;
$X^a$ or $Z^a$ = a group reducible to alkyl C 1 to 9, or a group reducible to phenyl-alkyl in which the alkyl group contains from 1 to 6 carbon atoms;
an adjacent pair of $X^a$, $Y^a$ and $Z^a$ form a chain substituted by one or two groups reducible to an alkyl C 1 to 6 group, (e) production of a compound of formula I in which $R_5$ is nitro, by nitration of a corresponding compound of formula I, or an ester thereof, in which $R_5$ is hydrogen, (f) production of a compound of formula I in which $R_5$ is amino by selective reduction of a corresponding compound of formula I, or an ester thereof, in which $R_5$ is nitro, (g) production of a compound of formula I in which $R_5$ is hydroxy, by hydrolysis of a corresponding compound of formula V,

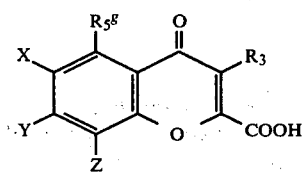

V or an ester thereof, in which
$R_3$, X, Y and Z are as defined above, and
$R_5{}^g$ is a group hydrolysable to an —OH group, (h) (i) production of a compound of formula I in which at least one of $R_5$, X or Z is chlorine, bromine or iodine, by reaction of a corresponding compound of formula VI,

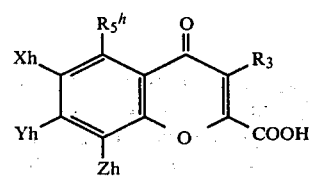

VI or an ester thereof, in which
$R_3$ is as defined above, and $R_5{}^h$, Xh, Yh and Zh have the same significances as $R_5$, X, Y and Z above, save that at least one of $R_5{}^h$, Xh and Zh represent a diazonium cation,
with cuprous chloride, cuprous bromide or an inorganic iodide respectively, (ii) production of a compound of formula I in which at least one of $R_5$, X or Z is halogen, by treating a corresponding compound of formula I, or an ester thereof, in which $R_5$, X or Z is another halogen, with an inorganic halide containing the desired halide ion, (iii) production of a compound of formula I in which at least one of $R_5$, X or Z is fluorine, by thermal decomposition of a fluoroborate or hexafluorophosphate salt of a corresponding compound of formula VI, (i) production of a compound of formula I in which one or both of $R_1$ and $R_2$ is alkyl C 1 to 6, by alkylation of a corresponding compound of formula I, or an ester thereof, in which $R_5$ is —$NR_1R_2$ and none or one of $R_1$ and $R_2$ is alkyl C 1 to 6, (j) production of a compound of formula I in which an adjacent pair of X, Y and Z form a chain —CH=CH—CH=CH—, which chain is optionally substituted by one or two alkyl C 1 to 6 groups, by aromatisation of a corresponding compound of formula I, or an ester thereof, in which an adjacent pair of X, Y and Z form a chain —$(CH_2)_4$—, which chain is optionally substituted by one or two alkyl C 1 to 6 groups, (k) production of a compound of formula I in which at least one of X, Z or $R_5$ is hydroxy-alkyl C 1 to 6, or in which $R_5$ is hydroxyalkoxy C 1 to 6, by
(i) selective reduction of a corresponding compound of formula VII,

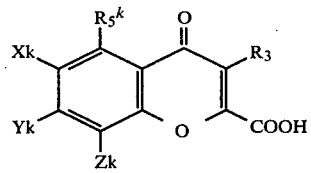

VII or an ester thereof, in which
$R_3$ is as defined above, and
$R_5{}^k$, Xk, Yk and Zk have the same significances as $R_5$, X, Y and Z, save that at least one of $R_5{}^k$, Xk and Zk represent a group reducible to hydroxy-alkyl C 1 to 6, or $R_5{}^k$ represents a group reducible to hydroxyalkoxy C 1 to 6, (ii) selective hydrolysis of a compound of formula VIII,

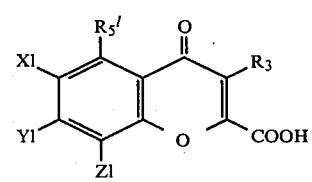

VIII or an ester thereof, in which
$R_3$ is as defined above, and
$R_5{}^l$, Xl, Yl and Zl have the same significances as $R_5$, X, Y and Z, save that at least one of $R_5{}^l$, Xl and Zl represent a group hydrolysable to hydroxy-alkyl C 1 to 6, or $R_5{}^l$ represents a group hydrolysable to hydroxyalkoxy C 1 to 6, (iii) production of a compound of formula I in which at least one of X, Z and $R_5$ is hydroxy-alkyl C 2 to 6, or $R_5$ is hydroxy-alkoxy C 2 to 6, by hydration of a corresponding compound of formula IX,

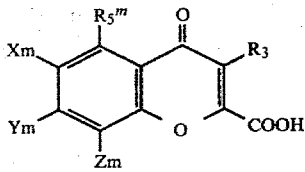
IX or an ester thereof, in which $R_3$ is as defined above, and $R_5^m$, Xm, Ym and Zm have the same significances as $R_5$, X, Y and Z, save that at least one of $R_5^m$, Xm and Zm is alkenyl C 2 to 6, or $R_5^m$ is alkenyloxy C 2 to 6, (l) production of a compound of formula I in which $R_5$ is —OH and X and Y, or Y and Z respectively, together form a chain, by subjecting a corresponding compound of formula I, or an ester thereof, in which Y and Z, or X and Y respectively, together form a chain and $R_5$ is —OH, to mildly basic, or to acidic conditions, (m) production of a compound of formula I in which $R_5$ is alkoxy C 1 to 6, alkenyloxy C 2 to 6 or alkanoyloxy C 2 to 6, or X or Z is alkoxy C 1 to 6-alkyl C 1 to 9, by alkylating, alkenylating or alkanoylating a corresponding compound of formula I, or an ester thereof, in which $R_5$ is —OH with a C 1 to 6 alkylating agent, a C 2 to 6 alkenylating agent or a C 2 to 6 alkanoylating agent, or by alkylating a corresponding compound in which X or Z is hydroxy-alkyl C 1 to 6 with a C 1 to 9 alkylating agent, (n) conversion of a compound of formula X,

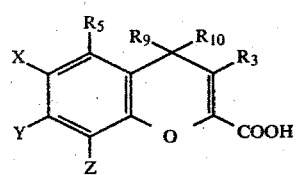
X or an ester thereof, in which $R_3$, $R_5$, X, Y and Z are as defined above, and $R_9$ and $R_{10}$ together form a =S or together form an —S(CH$_2$)$_n$S— chain, in which n is 2 or 3, to a corresponding compound of formula I, (o) production of a compound of formula I in which one of X and Z is alkenyl C 2 to 6 or phenyl alkenyl C 2 to 6, by condensation of a corresponding compound of formula XI,

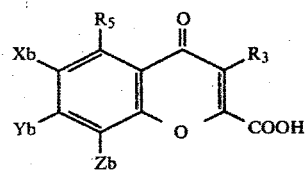
XI or an ester thereof, in which $R_3$ and $R_5$ are as defined above, and Xb, Yb and Zb have the same significances as X, Y and Z above, save that one of Xb and Zb is an oxo-substituted alkyl C 1 to 5 group, with a compound of formula XII, $$Q=CHR \qquad \text{XII}$$

in which

R is hydrogen, alkyl C 1 to 4 or phenyl-alkyl in which the alkyl contains from 1 to 4 carbon atoms, and Q is a trisubstituted phosphorous atom, (p) production of a compound of formula I in which X or Z is haloalkyl by reaction of a corresponding compound of formula I, or an ester thereof, in which X or Z is hydroxy-alkyl C 1 to 6, with a thionyl halide, or (q) production of a compound of formula I in which X or Z represents alkyl C 1 to 9 substituted by alkoxy C 1 to 6 by reacting a corresponding compound of formula I, or an ester thereof, in which X or Z represents alkyl C 1 to 9 substituted by a different alkoxy group or by hydroxy, with an appropriate C 1 to 6 alkanol, and if necessary or desired hydrolysing the ester of the compound of formula I to a compound of formula I and/or converting the compound of formula I to a pharmaceutically acceptable derivative thereof.

When $A_2$ is a group —OM the cyclisation of process (a)(i) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR" is preferably an ester group, e.g. R" may be a lower alkoxy group. When $A_2$ is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base for example an alkali metal, e.g. sodium, hydride. The reaction is preferably carried out at a temperature of from about 80° to 200° C., in the absence of free oxygen, e.g. under an inert atmosphere such as nitrogen.

The cyclisation of process (a)(ii) may be carried out by treating the compound of formula II with a cyclising agent, for example a dehydrating agent such as chlorosulphonic, polyphosphoric or sulphuric acid. The reaction is preferably carried out under anhydrous conditions and may be carried out at a temperature of from 0° to 100° C. Alternatively cyclisation may be achieved by converting the free carboxy groups of the compound of formula II to acyl halide groups and subjecting the resulting acyl halide to an intramolecular Friedel-Crafts reaction.

In process (b) the group D may be, for example an ester, acid halide, amide or a nitrile group, which may be hydrolysed to a —OOCH group. The hydrolysis may be carried out using conventional techniques, for example under mildly basic conditions, e.g. using sodium carbonate, sodium hydroxide, sodium bicarbonate, or under acidic conditions, e.g. a mixture of aqueous dioxan and hydrochloric acid, or hydrogen bromide in acetic acid. The hydrolysis may be carried out at a temperature of from about 25° to 120° C. depending on the compounds used. Alternatively the group D may be an alkyl, e.g. a lower alkyl such as methyl, a hydroxymethyl, an aralkenyl, e.g. styryl, an acyl, e.g. a lower alkanoyl such as acetyl, or a formyl group. The oxidation may be carried out using conventional techniques which do not otherwise modify the molecule to such an extent that the yield of the desired product is uneconomical, for example an alkyl or a hydroxymethyl group may be oxidised using selenium dioxide, e.g. under reflux in aqueous dioxan; or chromic acid, e.g. under reflux in aqueous acetic acid. Aralkenyl groups may be oxidised using, for example neutral or alkaline potassium permanganate in aqueous ethanol, and acyl groups may be oxidised using, for example chromic acid or an aqueous hypochlorite, e.g. sodium hypochlorite. The formyl group may be oxidised using, for example chromic acid or silver oxide.

When both A and B are hydrogen process (c) is a dehydrogenation and may be carried out by oxidation using a mild oxidising agent, for example selenium dioxide, palladium black, chloranil, lead tetraacetate or triphenyl methyl perchlorate. Alternatively the dehydrogenation of a compound of formula IV in which both A and B are hydrogen may be carried out indirectly by halogenation followed by dehydrohalogenation, e.g. by treatment with N-bromosuccinimide or pyridinium bromide perbromide to yield a compound of formula IV in which A is halogen and B is hydrogen, which is subsequently dehydrobrominated. When one of A and B is hydroxy the dehydration may be catalysed by an acid, e.g. sulphuric or oxalic acid; a base, e.g. potassium hydroxide; or a salt, e.g. potassium hydrogen sulphate; or N-bromosuccinimide. The reaction may be carried out in a solvent which is inert under the reaction conditions, e.g. a halogenated hydrocarbon, xylene, or glacial acetic acid. The reaction may be carried out at an elevated temperature, e.g. from 20° to 150° C.

In process (d) the reduction may be hydrogenation, e.g. catalytic hydrogenation, for example using a palladium on charcoal or a Raney nickel catalyst in a suitable solvent, e.g. ethanol when, as we prefer, the group to be reduced is an alkenyl, a phenylalkenyl, and alkenyloxy or an oxo-substituted alkyl group. The reaction may conveniently be carried out at from about 20° to 80° C., preferably at greater than atmospheric pressure. Alternatively when the group to be reduced is an oxo-substituted alkyl group, e.g. a propionyl group, the reduction may be carried out using a metal hydride, e.g. sodium borohydride, in a suitable solvent, e.g. water, at a temperature of from about 20° to 100° C. Thus in the starting material for process (d) we prefer at least one of $R_3^a$, $R_5^a$, $X^a$, $Y^a$ and $Z^a$ to be selected from the following significances:

$R_3^a$ = alkenyl C 2 to 6 or oxo-substituted alkyl C 1 to 6;
$R_5^a$ = alkenyloxy C 2 to 6, oxo-substituted alkoxy C 1 to 6, alkenyl C 2 to 6 or oxo-substituted alkyl C 1 to 6;
$X^a$ or $Z^a$ = alkenyl C 2 to 6, oxo-substituted alkyl C 1 to 6 or phenyl-alkenyl in which the alkenyl group contains from 2 to 6 carbon atoms;
an adjacent pair of $X^a$, $Y^a$ and $Z^a$ form a chain substituted by one or two alkenyl C 2 to 6 groups or substituted by one or two oxo-substituted C 1 to 6 alkyl groups.

The nitration of process (c) may be carried out using concentrated or fuming nitric acid optionally in combination with concentrated sulphuric acid. The reaction may be carried out in an excess of the nitrating agent or in a solvent which is inert under the reaction conditions, e.g. acetic acid or sulpholane. The reaction may be carried out at a temperature of from about 0° to 130° C. Especial care should be taken when this process is applied to a starting material containing an aldehyde, alkenyl or phenyl-alkenyl group.

The reduction of process (f) may be carried out by catalytic hydrogenation, e.g. using a palladium on charcoal (5% Pd) catalyst. The hydrogenation may if desired be carried out at a temperature of from about 10° to 50° C. and at an elevated pressure, e.g. of up to about 50 atmospheres. The hydrogenation may be carried out in a solvent which is inert under the reaction conditions, e.g. ethanol, acetic acid or a mixture thereof. The reduction may also be carried out by means of a chemical reducing agent, e.g. stannous chloride in acetic and hydrochloric acid, at a temperature of from about 20° to 100° C.

In process (g) $R_5^g$ may be an ether group —ORx in which Rx may be a straight or branched alkyl group, preferably containing from 1 to 10 carbon atoms, e.g. a methyl or a t-butyl group. Alternatively the group Rx may be a benzyl group, in which the phenyl is optionally substituted, e.g. by a nitro group. Alternatively the group —ORx may be part of a mixed acetal, for example —ORx may be a tetrahydropyranyl ether. The —ORx ether groups may be removed by treatment of the compound of formula V with acid in a solvent which is inert under the reaction conditions. Thus when Rx is a methyl or straight-chain alkyl group, the ether may be treated with an acid, for example hydrogen bromide, in for example water, glacial acetic acid or trifluoroacetic acid, at a temperature of from 0° C. to the boiling point of the solvent employed. When Rx is a branched chain alkyl group, for example t-butyl, the ether may be treated with an acid, for example hydrogen chloride, in for example methanol, usually at about ambient temperature. When Rx is a phenylalkyl or substituted phenylalkyl group, the ether may be treated with an acid, for example hydrogen bromide, in for example water, glacial acetic acid or trifluoracetic acid, at a temperature of from 0° C. to the boiling point of the solvent. Alternatively, the ether may be hydrogenolysed, for example in the presence of a palladium/carbon catalyst in for example ethanol or glacial acetic acid, at a temperature of from about 0° to 60° C. When Rx is part of a mixed acetal, the ether may be hydrolysed with an acid, for example 20% aqueous sulphuric acid, usually at about ambient temperature.

The group —ORx may also represent an ester group, for example of formula —OCORy, in which Ry may be hydrogen, an alkyl group preferably containing from 1 to 10 carbon atoms (e.g. methyl) and optionally substituted by halogen (e.g. trifluoromethyl); or a phenyl group. The removal of the ester group may be carried out under acidic, or preferably under basic conditions, using for example, sodium carbonate or sodium hydroxide, in for example water or ethanol, at temperatures ranging from 0° C. to the boiling point of the solvent employed.

$R_5^g$ may also be a diazo group, or a sulphonate group, for example a methane sulphonate or a p-toluene sulphonate group. The hydrolysis of the groups $R_5^g$, which are not groups —ORx, may be carried out under mildly basic conditions, for example using sodium hydroxide in a solvent which is inert under the reaction conditions, e.g. water or ethanol. Alternatively, when the group $R_5^g$ is a diazo group, the hydrolysis may be carried out using an aqueous acidic medium, e.g. aqueous sulphuric acid. The reaction may be carried out at a temperature of from about 0° C. to the boiling point of the solvent employed.

The reactions of process (h) are particularly relevant to the production of compounds of formula I in which only $R_5$ is halogen.

The reaction of process (h)(i) may be carried out in the presence of the corresponding halogen acid, in a solvent, e.g. water, at a temperature of between about 0° and 10° C. We prefer the iodide to be an alkali metal, e.g. potassium, iodide. When an iodide is used no halogen acid need be present.

Process (h)(ii) is particularly appropriate for the production of compounds of formula I in which $R_5$ is fluorine. The inorganic halide may be an alkali metal, e.g. a sodium or potassium, halide such as potassium fluoride. The reaction may be carried out in a solvent which is inert under the reaction conditions, e.g. acetone, ethanol or dimethylformamide. Alternatively the inorganic halide may be an appropriate cuprous halide and the solvent may be, for example dimethylsulphoxide or $\alpha$-picoline. The reaction may be carried out at a temperature of from about 20° C. to the boiling point of the solvent employed.

In process (h)(iii) the thermal decomposition may be carried out by subjecting the starting material, preferably in the absence of a solvent, to a temperature of from about 60° to 200° C.

Process (i) may be carried out using an appropriate alkyl halide, e.g. an alkyl iodide such as methyl iodide; an alkyl sulphate, e.g. dimethyl sulphate; a trialkoxonium borofluoride, e.g. triethyloxonium borofluoride; or an alkoxy sulphonyl fluoride, e.g. methoxysulphonylfluoride. The use of a trialkoxoxonium borofluoride can only lead to mono-alkylamino products. The reaction may be carried out in a solvent which is inert under the reaction conditions, e.g. acetone or methylene chloride. The reaction may be carried out at a temperature of from about $-20°$ C. to the boiling point of the solvent employed, e.g. about 35° C. When the alkyl group desired is a methyl group the reaction may be carried out using formaldehyde and formic acid under reflux.

The selective dehydrogenation of process (j) may be effected by means of a suitable dehydrogenating agent, e.g. sulphur, selenium, or a metal catalyst, e.g. platinum or palladium. The metal catalyst may conveniently be used in the form of the finely divided metal adsorbed onto carbon, e.g. 10% PD/C. The reaction may be carried out either in the absence of a solvent or in a high boiling solvent, which is inert under the reaction conditions, e.g. naphthalene or quinoline. The reaction may be carried out at an elevated temperature, e.g. of from about 230° to 350° C. The reaction is preferably carried out using an ester starting material.

In process (k)(i) we prefer one of $R_5^k$, Xk and Zk to represent epoxide substituted C 2 to 6 alkyl or an oxo-substituted C 1 to 6 alkyl group or $R_5^k$ to represent epoxide substituted C 2 to 6 alkoxy or oxo-substituted C 1 to 6 alkoxy. The reduction may be carried out using a metal hydride, for example a borohydride such as sodium borohydride. The reaction may be carried out in a suitable solvent, for example water, bis(2-methoxyethyl)ether or a mixture thereof, and may conveniently be carried out at a temperature of from about 0° to 40° C. Alternatively the reduction may be carried out using hydrogen and a catalyst, e.g. palladium on carbon. The catalytic reduction may be carried out in a suitable solvent, e.g. ethanol, at a temperature of from about 20° to 100° C.

In process (k)(ii) we prefer at least one of $R_5^l$, Xl and Zl to represent a halo-alkyl C 1 to 6 group or, when a di-hydroxy-alkyl group is required, an epoxy-alkyl C 2 to 6 group; or $R_5^l$ to represent halo-alkoxy C 1 to 6. When a halo-hydroxy alkyl group is desired the hydrolysis of the epoxy-alkyl group may be carried out in the presence of an appropriate halogen acid, e.g. HCl. The hydrolysis may, for example, be carried out under mildly basic conditions, e.g. using sodium hydroxide, in a suitable solvent, e.g. ethanol or aqueous dioxan. The reaction may be carried out in the presence of a silver salt, e.g. silver acetate, and may be carried out at a temperature of from about 20° to 100° C.

In process (k)(iii) the hydration may, for example, be carried out under acidic conditions, e.g. aqueous sulphuric acid; or using a combination of a borane and a peroxide, e.g. hexyl borane and hydrogen peroxide; or using a mercury compound in combination with a reducing agent, e.g. mercuric acetate and sodium borohydride. The reaction may be carried out in the absence of a solvent, or in a suitable solvent e.g. water. The reaction may be carried out at a temperature of from about 20° to 100° C.

Process (l) is a Wesseley-Moser rearrangement and is preferably carried out in an aqueous organic solvent, e.g. aqueous ethanol, and under acidic (e.g. HI) or weakly basic (e.g. $NaHCO_3$ or $Na_2CO_3$) conditions. The reaction is preferably carried out at a temperature of from about 20° to 100° C. The reaction passes through an intermediate of formula II(i).

In process (m) the alkylating or alkenylating, agent may be a compound R-L in which R is alkyl C 1 to 6, or alkenyl C 2 to 6 and the alkanoylating agent may be a compound RyCOL in which Ry is alkyl C 1 to 5, L being a good leaving group, e.g. an anion forming group. Suitable anion forming groups include, for example, a halide, e.g. a bromide or iodide, or a sulphate, or, when an alkanoylating compound RyCOL is used, a sulphonate group. When an alkanoylating agent RyCOL is used L may also represent an alkyl ether group, e.g. a pivaloyl group. The reaction may be carried out in a suitable solvent, e.g. a lower alkanol such as ethanol; a ketone such as acetone or isobutylmethyl ketone; dimethylformamide or aqueous dioxan. The reaction may also be carried out in the presence of an acid binding agent, e.g. potassium carbonate, and optionally also in the presence of a catalyst, e.g. potassium iodide; suitably the reaction is carried out at a temperature of 25° to 150° C. Alternatively process (m) may be carried out using the starting compound of formula I (or preferably an ester thereof), in the form of a salt, e.g. a thallium or sodium salt of the hydroxy group. When a thallium salt is used the reaction may be carried out at an elevated temperature without a solvent or in a solvent which is inert under the reaction conditions, e.g. ethanol or dimethylformamide, and the product may be recovered from the reaction mixture by solvent extraction.

In processes (n), when $R_9$ and $R_{10}$ together form a chain $-S-(CH_2)_n-S-$, the conversion may comprise oxidative hydrolysis and may be carried out in an aqueous polar organic solvent, for example aqueous ethanol, acetone or tetrahydrofuran. The oxidative hydrolysis may be carried out in the presence of an oxidising agent, for example mercuric chloride, an N-halosuccinimide such as N-bromo- or N-chloro-succinimide, a per-acid such as periodic acid; or p-toluenesulphonchloramide or a salt thereof. When mercuric chloride is used the reaction may be carried out in the presence of a base, e.g. mercuric oxide, cadmium carbonate or calcium carbonate. N-halosuccinimides may be used alone or in the presence of a silver salt, e.g. silver perchlorate, or silver nitrate. The reaction may conveniently be carried out at a temperature of from about 15° to 100° C.

When $R_9$ and $R_{10}$ together form a —S group the conversion may comprise (oxidative) hydrolysis and may be carried out in the presence of a heavy metal compound, e.g. a compound of group Ib, IIb or IIIb of the Periodic Table of Mendeleef, as catalyst. Suitable compounds include mercury, thallium and silver compounds, e.g. mercury (II) acetate or chloride, thallium (III) trifluoroacetate, or silver oxide. The reaction may be carried out in the presence of water and an organic solvent system such as acetone-acetic acid, alkanols, tetrahydrofuran/methanol, or tetrahydrofuran. Alternatively the reaction may be carried out by alkylation followed by hydrolysis. In such cases the reaction may be effected by (i) an alkyl halide or sulphonate (e.g. methyl iodide), in a moist solvent, e.g. acetone, (ii) an alkylfluorosulphonate and water in sulphur dioxide, or (iii) a trialkyl oxonium fluoroborate followed by aqueous sodium hydroxide.

Process (o) is a Wittig synthesis and may be carried out in a solvent which is inert under the reaction conditions, e.g. dimethylsulphoxide, xylene, diethyl ether, tetrahydrofuran or a lower alkanol such as ethanol. The reaction may be carried out at a temperature of from about 20° C. to the boiling point of the solvent employed. The reaction may be catalysed by a base, e.g. sodium hydride or lithium ethoxide. We prefer the group Q to be $(C_6H_5)_3P$ or $(C_2H_5O)_2OP$.

In process (p) the reaction may be carried out in a solvent which is inert under the reaction conditions, e.g. a halogenated hydrocarbon solvent such as chloroform, or dichloromethane. The thionyl halide may be, for example, thionyl chloride. The reaction may be carried out at a temperature of from about 20° to 90° C.

The alkoxide exchange of process (q) may be effected under, for example, acidic conditions, e.g. in the presence of hydrochloric acid, or may be effected under basic conditions, e.g. in the presence of the alkoxide ion corresponding to the desired alkoxy group. The reaction is preferably conducted in an excess of the alkanol corresponding to the desired alkoxy group, at a temperature of from about 20° C. to the boiling point of the reaction mixture, e.g. about 160° C.

In processes (c) to (q) inclusive the ester may be, for example, a C 1 to 10 alkyl ester.

The compounds of formula II, in which $A^1$ and $A^2$ represent the groups —COCHR$_3$COCR″ nnd —OM or halogen, may be made by reacting a compound of formula XV,

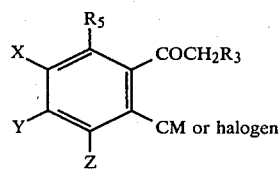

in which $R_3$, $R_5$, X, Y, Z, and M are as defined above, with a compound of formula XVI,

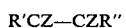R'CZ—CZR″     XVI in which R″ is as defined above,

R' is a suitable leaving group, e.g. an alkoxy, halo, amino, alkylamino, substituted amino (e.g. an arylsulphonylamino group) or substituted alkylamino group, reactive with the carbanion of the —COCH$_2$R$_3$ group of the compound of formula XV, and each Z is a carbonyl oxygen atom, or one Z may represent two halogen atoms and the other a carbonyl oxygen atom, and if necessary hydrolysing the resulting compound to a compound of formula II. The preferred compounds of formula XVI are dialkyl oxalates, e.g. diethyl oxalate.

The compounds of formula III may be made in a manner analogous to process (a)(i) using a starting material of formula XVII,

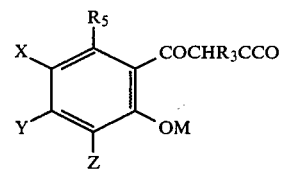

in which $R_3$, $R_5$, X, Y, Z, M and D are as defined above.

The compounds of formula XVII may be made from known compounds in a manner analogous to that described above for the preparation of the corresponding compounds of formula II, using a compound of formula R'COD in which R' and D are as defined above, in place of the compound of formula XVI.

Alternatively the compounds of formula III may, for example in the case of the acid halide, the amide and the nitrile, be made from compounds of formula I using conventional techniques, e.g. reaction of an ester of the compound of formula I with ammonia to produce the amide, followed by dehydration of the amide to form the nitrile.

The compounds of formula IV in which both A and B are hydrogen may be made by cyclising a compound of formula XVIII,

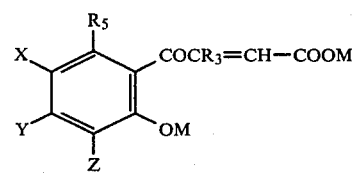

in which $R_3$, $R_5$, X, Y, Z and M are as defined above, by treating the compound of formula XVIII with a base in a solvent which is inert under the reaction conditions.

The compounds of formula XVIII may be made by reacting a compound of formula XV carrying a group —OM, with glyoxalic acid or an ester thereof. Alternatively the compounds of formula XVIII in which $R_3$ is hydrogen may be made by reacting a compound of formula XIX,

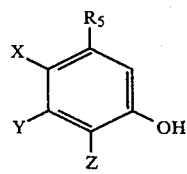

in which $R_5$, X, Y and Z are as defined above, with maleic anhydride in a solvent in the presence of a Lewis acid, e.g. AlCl₃, and decomposition of the resulting complex with dilute acid.

The compounds of formula IV in which both A and B are hydrogen may also be made by selective hydrogenation of a corresponding compound of formula I.

The compounds of formula IV in which one of A and B is halogen may be made by halogenation of a corresponding compound of formula IV in which both A and B are hydrogen. The compounds of formula IV in which one of A and B is —OH may be made by treating a compound of formula II(i) in which $A^2$ is —OM with one equivalent of an inorganic acid, e.g. hydrochloric acid, in an inert solvent, e.g. ethanol, at a temperature of from about 20° to 80° C.

The compounds of formula VI may be made by conventional techniques from a corresponding compound of formula XXI,

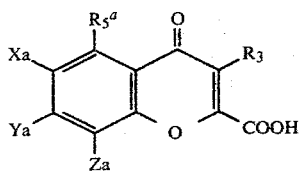

or an ester thereof, in which
$R_3$ is as defined above, and
$R_5{}^a$, Xa, Ya and Za have the same significances as $R_5$, X, Y and Z above, save that at least one of $R_5{}^a$, Xa and Za represent an —NH₂ group.

The compounds of formula II in which $A^1$ and $A^2$ represent —H and —O—C(COR″)=CH—COR″ may be made by reacting a compound of formula XIX, with a dialkyl acetylene dicarboxylate, in conventional manner, followed if necessary by hydrolysis of the reaction product. Compounds of formula II in which $A^1$ and $A^2$ represent —H and —O—C(COR″)=CR₃—COR″ and may be made by reaction of a compound of formula XIX with an appropriate halo fumarate of formula R″OC(R₃)C=C(halogen)COR″ in which R₃ and R″ are as defined above. The halo fumarates may be made by dehydrogenation of the corresponding dihalosuccinic acid derivative.

The compounds of formulae XX, V, VII, VIII, IX (some of which are compounds of formula I) and XI may be made by processes analogous to process (a) using starting materials which are known or which may be made from known compounds using conventional techniques. Alternatively some of these compounds may be made by other conventional techniques from known compounds or from compounds described in this specification, e.g. the compounds of formula VII having an epoxide substituent may be made by reacting the corresponding compound having an alkenyl substituent with a per acid. Compounds of formula X may be made by reacting a compound of formula I with a compound of formula HS(CH₂)ₙSH in which n is as defined above, or with phosphorus pentasulphide.

The compounds of formulae X, XII, XV, XVI and XIX are either known or may be made from known compounds using conventional techniques.

The compounds of formula I and the intermediates therefore may be isolated from their reaction mixtures using conventional techniques.

Pharmaceutically acceptable derivatives of the compounds of formula I include pharmaceutically acceptable salts, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the β-(diethylamino)-ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl) ether, e.g. the bis-2-oxapropan-1,3-diyl ester. The pharmaceutically acceptable acid addition salts of the basic esters, and also of those compounds in which $R_5$ is a group —NR₁R₂, e.g. the hydrochloride, the hydrobromide, the oxalate, the maleate or the fumarate may also be used. The esters may be made by conventional techniques, e.g. esterification, transesterification or reaction of the acid, or a salt thereof, with an appropriate compound containing a good leaving group. The amides may be, for example, unsubstituted or mono- or di-C 1 to 6 alkyl amides and may be made by conventional techniques, e.g. reaction of an ester of the corresponding acid with ammonia or an appropriate amine.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen e.g. the combination of reaginic antibody with specific antigen (see Example 27 of British Patent-Specification No. 1,292,601). In man, both subjective and objective changes which result from the inhalation of specific antigen by sensitised subjects are inhibited by prior administration of the new compounds. Thus the new compounds are useful in the treatment of asthma, e.g. allergic asthma. The new compounds are also useful in the treatment of so-called 'intrinsic' asthma (in which no sensitivity to extrinsic antigen can be demonstrated). The new compounds are also useful in the treatment of other conditions in which antigen-antibody reactions are responsible for disease, for example, hay fever; certain eye conditions, e.g. trachoma; alimentary allergy, e.g. urticaria and atopic eczema; and gastrointestinal allergy, especially in children, e.g. milk allergy.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example 27 of British Patent Specification No. 1,292,601. For man the indicated total daily dosage is in the range of from 1 mg to 3,500 mg preferably from 1 mg to 3,000 mg and more preferably from 1 mg to 600 mg, which may be administered in divided doses from 1 to 6 times a day or in sustained release form. Thus unit dosage forms suitable for administration (by inhalation or oesophageally) comprise from 0.17 mg to 600 mg, preferably 0.17 mg to 500 mg and more preferably from 0.17 mg to 100 mg of the compound preferably admixed with a solid or liquid pharmaceutically acceptable diluent, carrier or adjuvant.

The compounds of formula I, and pharmaceutically acceptable derivatives thereof have the advantage that they are more efficacious in certain pharmacological models, or are more readily absorbed (as evidenced by plasma level, or by the ratio of the activity of the compounds when administered intestinally and intravenously in the test set out in Example 27 of British Patent Specification No. 1,292,601), or are longer acting as measured by plasma half-life or are more active when administered oesophageally than compounds of similar structure to the compounds of formula I.

Preferred values of the substituents in formula I are:

$R_3$=hydrogen; or straight or branched alkyl C 1 to 4, e.g. methyl or propyl;

$R_5$=hydrogen; hydroxy; alkoxy C 1 to 3, e.g. methoxy or propoxy; acetoxy; allyloxy; nitro; amino; mono- or di-alkyl C 1 to 4 amino, e.g. dimethylamino or mono-ethylamino; chlorine or fluorine; straight or branched alkyl C 1 to 4, e.g. methyl; hydroxy-alkyl C 1 to 4, e.g. hydroxy-methyl; or hydroxy-alkoxy C 1 to 4, e.g. 2-hydroxy-propoxy, an adjacent pair of X, Y and Z (and more preferably X and Y) form a chain —(CH$_2$)$_4$—, —CH=CH—CH=CH—, —OCH$_2$CH$_2$CH$_2$—, or such a chain substituted by one or two methyl or ethyl groups, and the remaining substituent X or Z represents hydrogen; straight, branched or cyclo alkyl C 1 to 8, e.g. ethyl, n-propyl, n-hexyl, cyclopentylethyl, or cyclopentylmethyl; allyl or hex-1-enyl; halogen, e.g. bromine or chlorine; mono- or di-hydroxyalkyl C 1 to 4, e.g. 2-hydroxy-propyl; chloro-alkyl C 1 to 4, e.g. chloropropyl; chloro-hydroxyalkyl C 1 to 4, e.g. chloro-hydroxypropyl; oxo-substituted alkyl C 1 to 4, e.g. formyl, propionyl or 3-oxo-butyl; phenyl-alkyl in which the alkyl contains from 1 to 3 carbon atoms, e.g. benzyl or phenylethyl; styryl; or alkoxy C 1 to 4-alkyl C 1 to 4, e.g. ethoxy-methyl.

Particularly preferred compounds are those in which $R_3$ is hydrogen, $R_5$ is hydrogen, hydroxy, amino, mono- or di-alkyl amino, fluorine or alkoxy and the substituent X or Z which does not form part of a chain is propyl and an adjacent pair of X, Y and Z form a —(CH$_2$)$_4$— or —CH=CH—CH=CH— chain.

Especially preferred compounds of formula I are those in which $R_5$ is hydrogen, hydroxy, —NH$_2$, —N(CH$_3$)$_2$, —NHC$_2$H$_5$, fluorine, chlorine or methoxy.

We prefer the free acids of formula I.

As a specific group of compounds of formula I we provide those in which $R_3$ is hydrogen, $R_5$ is hydrogen, alkyl or hydroxy, X and Y together form a —(CH$_2$)$_4$— chain and Z is alkyl, alkenyl or halogen. As a further specific group of compounds we provide those of formula I in which $R_3$ is hydrogen, $R_5$ is hydrogen, hydroxy, nitro, —NR$_1$R$_2$ or halogen, X and Y together form a —(CH$_2$)$_4$— chain and Z is alkyl or alkenyl.

According to the invention there is also provided a process for the production of a pharmaceutically acceptable salt of a compound of formula I, which comprises treating a compound of formula Ic,

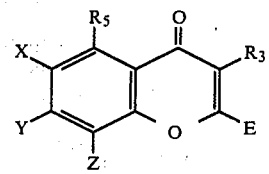

in which $R_3$, $R_5$, X, Y and Z are as defined above, and

E is a carboxylic acid group (or an ester thereof, or another salt thereof), a nitrile group, an acid halide group or an amide group, with a compound containing an available pharmaceutically acceptable cation and capable of converting the group E to a pharmaceutically acceptable salt of a carboxylic acid group.

Compounds capable of converting the group E to a pharmaceutically acceptable salt of a carboxylic acid group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process with an appropriate salt. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

According to our invention we also provide a pharmaceutical composition comprising (preferably less than 80% and more preferably less than 50% by weight) of a compound of formula I, or a pharmaceutically acceptable derivative thereof, in combination with a pharmaceutically acceptable adjuvant, diluent or carrier. Examples of suitable adjuvants, diluents or carriers are:- for tablets capsules and drageés; microcrystalline cellulose, calcium phosphate, diatomaceous earth, a sugar such as lactose, dextrose or manaitol, talc, stearic acid, starch, sodium bicarbonate and/or gelatin; for suppositories, natural or hardened oils or waxes; and for inhalation compositions, coarse lactose. The compound of formula I, or the pharmaceutically acceptable derivative thereof, preferably is in a form having a mass median diameter of from 0.01 to 10 microns. The compositions may also contain suitable preserving, stabilising and wetting agents, solubilizers, sweetening and colouring agents and flavourings. The compositions may, if desired, by formulated in sustained release form. We prefer compositions which are designed to be taken oesophageally and to release their contents in the gastrointestinal tract.

Some of the compounds of formula I are asymetric and may therefore exist in the form of two (or more) optical isomers or a racemic or other mixture of such isomers. The various optical isomers may be resolved, wholly or partially, using conventional techniques, e.g. formation of a salt with an optically active base, e.g. cinchonidine, fractional crystallisation of the salt and subsequent regeneration of the free acid.

The invention is illustrated, but in no way limited by the following Examles, in which the temperatures are in °C.

EXAMPLE 1

6,7,8,9-Tetrahydro-1-oxo-10-propyl-4H-naphtho[2,3-h]pyran-2-carboxylic acid (a) 6-Acetyl-7-allyloxy-1,2,3,4-tetrahydronaphthalene A mixture of 6-acetyl-7-hydroxy-1,2,3,4-tetrahydronaphthalene (2.0 g), allyl bromide (1.7 g), anhydrous potassium carbonate (2.2 g) and N,N-dimethylformamide (50 ml) was stirred at room temperature for 24 hours. The mixture was then poured into ice/water (400 ml) and stirred. The precipitate was filtered off, washed with water and then dried to leave, as an off-white powder, 6-acetyl-7-allyloxy-1,2,3,4-tetrahydronaphthalene (2.38 g), mp 62°–63°.

(b) 7-Acetyl-5-allyl-6-hydroxy-1,2,3,4-tetrahydronaphthalene

The product of step (a) (60.2 g) was heated in a fluidised sand-bath from 140°–200° during 1 hour and was then further heated at 200° for 7 hours. The substance was allowed to cool and subsequently there was recovered as a brown oil, 7-acetyl-5-allyl-6-hydroxy-1,2,3,4-tetrahydronaphthalene (58.6 g).

(c) 7-Acetyl-6-hydroxy-5-propyl-1,2,3,4-tetrahydronaphthalene

5% Palladium/carbon catalyst (9 g) was added to a solution of the product of step (b) (115 g) in ethanol (500 ml). The mixture was shaken with hydrogen at an overpressure of 4 to 5 psi at room temperature for 1 hour. The catalyst was removed by filtration and the filtrate concentrated and cooled. The precipitated solid was filtered off and dried to give 7-acetyl-6-hydroxy-5-propyl-1,2,3,4-tetrahydronaphthalene (96 g), mp 52°–53°.

(d) Ethyl 6,7,8,9-tetrahydro-4-ono-10-propyl-4H-naphtha[2,3-b]pyra-2-carboxylate To a stirred solution of sodium ethoxide in ethanol, prepared from sodium (89.3 g) and ethanol (2.7 l) was added a solution of the product of step (c) (150 g) and diethyl oxalate (283 g) in ethanol (500 ml). The mixture was stirred and heated under reflux for 4 hours and then, after cooling, was poured into a stirred mixture of concentrated hydrochloric acid (500 ml), water (10 l) and chloroform (1.5 l). The chloroform layer was separated and combined with a chloroform (1.5 l) wash of the aqueous layer. The chloroform solution was washed with water and then evaporated to a brown oil. A solution of this oil in ethanol (1 l) containing concentrated hydrochloric acid (1.5 ml) was heated under reflux for 1 hour. On concentrating and cooling a precipitate was obtained. This precipitate was filtered off and the solid recrystallised from ethanol to give ethyl 6,7,8,9-tetrahydro-4-oxo-10-propyl-4H-naphtho[2,3b]pyran-2-carboxylate (201 g), mp 98°–99.5°.

(e) Sodium 6,7,8,9-tetrahydro-4-oxo-10-propyl-4H-naphtho[2,3-b]pyran-2-carboxylate A mixture of the product of step (d) (9.5 g) and sodium bicarbonate (2.8 g) in methanol (60 ml), and water (100 ml), was heated under reflux for 1.5 hours. The mixture was evaporated and the residue was dissolved in water (500 ml). The solution was filtered, then acidified with hydrochloric acid and the resulting precipitated acid was filtered off, washed with water, dried and recovered as a white solid (8.2 g), which was dissolved in a solution of sodium bicarbonate (2.37 g) in water (50 ml). The solution was filtered, evaporated to low bulk and diluted with acetone. The solution crystallised upon cooling and scratching and gave, as a white powder, sodium 6,7,8,9-tetrahydro-4-oxo-10-propyl-4H-naphtho[2,3-b]pyran-2-carboxylate (4.9 g).

(f) 6,7,8,9-Tetrahydro-4-oxo-10-propyl-4H-naphtho[2,3-b]pyran-2-carboxylic acid

A solution of the product of step (c) (0.3 g), in water (25 ml) was acidified with 2 N hydrochloric acid. The precipitated organic acid was filtered off washed with water and dried to give the title compound as a white solid, (0.2 g), mp 245°–8°.

EXAMPLE 2

Ethyl 6,7,8,9-tetrahydro-4-oxo-10-propyl-4H-naphtho[2,3-b]pyran-2-carboxylate

A stirred solution of the product of Example 1(c) (5.75 g) and diethyl oxalate (7.3 g) in petroleum ether (60°–80°) (50 ml) was treated portionwise over 2 minutes with sodium hydride, (2.8 g of a 50% w/w suspension in oil). When effervescence subsided the mixture was stirred and heated under reflux for 10 minutes, cooled and treated with a solution of hydrogen chloride in ethanol (35 ml). This mixture was heated under reflux for 5 minutes then it was cooled, diluted with chloroform and sodium chloride was filtered off. The filtrate was evaporated and the residue was extracted into boiling petroleum ether (40°–60°). The petroleum ether extract was filtered, concentrated and cooled and crystallisation occurred. The product was filtered off and recovered as a cream solid, identified by mass spectroscopy, nuclear magnetic resonance spectroscopy and by thin layer chromatography as the title compound (6.0 g), mp 98°–99.5°.

EXAMPLE 3

Ethyl 6,7,8,9-tetrahydro-4-oxo-10-propyl-4H-naphtho[2,3b]-pyran-2-carboxylate (a) Ethyl 10-allyl-6,7,8,9-tetrahydro-4-oxo-4H-naphtho[2,3b]pyran-2-carboxylate The product of Example 1(b) (58.6 g) was treated with sodium (29.4 g) and diethyl oxalate (93.1 g) in ethanol (1 l) using the conditions described in Example 1(d) to give ethyl 10-alkyl-6,7,8,9-tetrahydro-4-oxo-4H-naphtho[2,3b]pyran-2-carboxylate (50.2 g), as a pale yellow solid, mp 98°–101°.

(b) Ethyl 6,7,8,9-tetrahydro-4-oxo-10-propyl-4H-naphtho[2,3-b]pyran-2-carboxylate A solution of the product of step (a) (20 g), in ethanol (120 ml), was treated with a 5% palladium on charcoal catalyst (100 mg), and shaken in a hydrogen atmosphere at 45 psi for 2 hours at room temperature. The catalyst was subsequently filtered off and the filtrate was evaporated. The residue solidified upon trituration with a little diethyl ether and the solid was twice crystallised from aqueous ethanol to give as white crystals, ethyl 6,7,8,9-tetrahydro-4-oxo-10-propyl-4H-naphtho[2,3-b]pyran-2-carboxylate (10 g), mp 98°–99.5°.

EXAMPLE 4

10-Ethyl-6,7,8,9-tetrahydro-4-oxo-4H-naphtho[2,3b-]pyra-2-carboxylic acid (a) 5-Ethyl-6-hydroxy-1,2,3,4-tetrahydronaphthalene 5-Acetyl-6-hydroxy-1,2,3,4-tetrahydronaphthalene (15.0 g) was heated at reflux in a mixture of dioxan (40 ml) and 50% HCl (50 ml) containing zinc amalgam (16.0 g) for 18 hours. The mixture was cooled, filtered and the filtrate was extracted with ether. The ether extracts were washed with water, dried (MgSO₄), filtered and evaporated to dryness leaving a solid which crystallised from petroleum ether (60°–80°) to give 5-ethyl-6-hydroxy-1,2,3,4-tetrahydronaphthalene as pale yellow needles, 13.5 g (97%), mp 94°–5°.

(b) Methyl 10-ethyl-6,7,8,9-tetrahydro-4-oxo-4H-naphtho[2,3b]pyran-2-carboxylate A solution of the product of step (a) (12.7 g), dimethylacetylene dicarboxylate (10.2 g) n dioxan (50 ml) containing 'Triton B' (40% aqueous solution of benzyltrimethylammonium hydroxide, 10 drops) was heated on a steam bath for 20 minutes. Water (100 ml) was added and the mixture was extracted with ether. The extracts were dried (MgSO₄), filtered and the filtrate was evaporated to dryness. This left, as an orange oil, a mixture of the maleate and fumarate esters. (Nuclear magnetic resonance spectroscopy showed a predominance of the fumarate, the isomer required for cyclisation to the chromone derivative).

This mixture of maleate and fumarate (19.7 g) was heated at 100° in polyphosphoric acid (200 g) for 18 hours. The mixture was poured into ice and the resulting solution was extracted with ethyl acetate. The organic extracts were washed well with water, dried (MgSO₄), filtered and evaporated to dryness leaving an oil. This oil was taken up in ether and cooled to 0° when methyl 10-ethyl-6,7,8,9-tetrahydro-4-oxo-4H-naphtho[2,3-b]pyran-2-carboxylate crystallised as off-white needles, 3.3 g.

(c) 10-Ethyl-6,7,8,9-tetrahydro-4-oxo-4H-naphtho[2,3-b]pyran-2-carboxylic acid

A mixture of the product of step (b) (3.0 g) and sodium bicarbonate (3.0 g) in water (100 ml) was heated at reflux for 3 hours. The solution was cooled and acidified and the resulting white solid was filtered and dried to give the title compound 2.4 g (84%), mp 269°–271°.

(d) Sodium 10-ethyl-6,7,8,9-tetrahydro-4-oxo-4H-naphtho[2,3-b]pyran-2-carboxylate The product of step (c) (2.14 g) was dissolved in a solution of sodium bicarbonate (0.66 g) in water (50 ml). The resulting solution was filtered and freeze-dried leaving an off-white solid which was further dried in vacuo at 30° giving the desired sodium salt (95%).

EXAMPLE 5

6,7,8,9-Tetrahydro-5-nitro-4-oxo-10-propyl-4H-naphtho[2,3-b]pyran-2-carboxylic acid (a) Ethyl 6,7,8,9-tetrahydro-5-nitro-4-oxo-10-propyl-4H-naphtho[2,3-b]pyran-2-carboxylate Ethyl 6,7,8,9-tetrahydro-4-oxo-10-propyl-4H-naphtho[2,3-b]pyran-2-carboxylate (9.4 g) was dissolved in concentrated sulphuric acid (100 ml) and cooled to room temperature, and fuming nitric acid (3 ml) was added dropwise, with stirring. The resulting mixture was stirred for a further 3 hours and then poured into water (2 l). The resulting yellow semi-solid was extracted into ether. The organic layer was washed with water, dried (sodium sulphate) and evaporated to give a yellow solid of moderately pure ethyl 6,7,8,9-tetrahydro-5-nitro-4-oxo-10-propyl-4H-naphtho[2,3-b]pyran-2-carboxylate (3.5 g; 79%). An analytically pure sample (5 g) was obtained on recrystallisation from cyclohexane, mp 140°–2°.

(b) 6,7,8,9-Tetrahydro-5-nitro-4-oxo-10-propyl-4H-naphtho[2,3-b]pyran-2-carboxylic acid The ester product of step (a) (720 mg) and sodium bicarbonate (200 mg) in water (10 ml) and ethanol (5 ml) were heated under reflux for 2 hours. The ethanol was removed and the aqueous solution was made up to 50 ml with water, and acidified producing a semi-solid precipitate. The solid was recrystallised from ethanol to give an off-white solid shown to be an analytically pure sample of the title acid, mp 265°–7° (decomposition 261°). Yield 220 mg (33%).

(c) Sodium 6,7,8,9-tetrahydro-5-nitro-4-oxo-10-propyl-4H-naphtho[2,3-b]pyran-2-carboxylate The acid product of step (b) above (0.2 g) was converted into the corresponding sodium salt (0.15 g), by the method described in Example 4(d).

EXAMPLE 6

5-Amino-6,7,8,9-tetrahydro-4-oxo-10-propyl-4H-naphtho[2,3-b]pyran-2-carboxylic acid (a) Ethyl 5-amino-6,7,8,9-tetrahydro-4-oxo-10-propyl-4H-naphtho[2,3-b]pyran-2-carboxylate The product of Example 5(a) (20 g) in ethanol (150 ml) and acetic acid (150 ml) was hydrogenated for 2 days at 30 psi and room temperature using 5% palladium on charcoal (2 g) as catalyst. The reaction mixture was filtered through a super-cel filter aid and the filtrate was evaporated. The crude product was treated with water (1 l) and ether (1 l) and transferred to a separating funnel. The ether layer was run off, washed with water (1 l), saturated aqueous sodium bicarbonate solution (3×500 ml), water (1 l), dried (sodium sulphate) and evaporated to yield a red solid (18 g). This solid was recrystallised from petroleum ether (40°–60°) to give rod needles of a pure sample of the title ester (13.1 g; 71.5%), mp 78°–81°.

(b) Sodium 5-amino-6,7,8,9-tetrahydro-4-oxo-10-propyl-4H-naphtho[2,3-b]pyran-2-carboxylate The ester of step (a) (4.5 g) was converted into its corresponding sodium salt (3.2 g) by the method of Example 1(c).

(c) 5-Amino-6,7,8,9-tetrahydro-4-oxo-10-propyl-4H-naphtho[2,3-b]pyran-2-carboxylic acid The salt of step (b) (3.0 g) was converted into the corresponding acid (2.5 g) mp 285° (decomp) by the method of Example 1(f).

EXAMPLE 7

5-Amino-6,7,8,9-tetrahydro-4-oxo-10-propyl-4H-naphtho[2,3-b]pyran-2-carboxylic acid Stannous chloride dihydrate (132 g) was dissolved in concentrated HCl (400 ml) and to this solution was added the product of Example 5(a) (30 g) followed by glacial acetic acid (400 ml). The whole mixture was heated on a steam bath for 2 hours, poured onto ice water (1,500 ml) and the precipitated solid was filtered, washed with water and dried in vacuo at 95° to give 5-amino-6,7,8,9-tetrahydro-4-oxo-10-propyl-4H-naphtho[2,3-b]pyran-2-carboxylic acid as an orange solid, (21 g; 84%) mp 285° (decomp).

EXAMPLE 8

(a) 6,7,8,9-Tetrahydro-5-hydroxy-4-oxo-10-propyl-4H-naphtho[2,3-b]pyran-2-carboxylic acid The product of Example 6(a) (6.0 g) in 50% (v/v) sulphuric acid (30 ml) at 0° was treated, whilst being stirred, over 15 minutes with a solution of sodium nitrite (1.4 g) in water (10 ml). Stirring at 0° was continued for 30 minutes, then the solution was poured, in aliquots, into a 50% (v/v) sulphuric acid solution at 120° over a period of 20 minutes. The reaction mixture was allowed to warm slowly (over 30 minutes) to 140° after which time it was cooled to room temperature. The solution was extracted with chloroform and both layers were filtered through a super-cel filter aid. The chloroform layer was treated with saturated sodium bicarbonate precipitating the sodium salt of the 5-hydroxy acid. The red-brown solid was filtered off and combined with the bicarbonate washings and a second bicarbonate extract of the chloroform layer. This suspension was treated with concentrated hydrochloric acid to precipitate the free acid, which was extracted back into chloroform (5×100 ml). The chloroform extracts were combined and washed with water, dried (sodium sulphate) and evaporated to yield a yellow solid (2.8 g; 51%). A pure sample of the title compound (2.1 g; 38.2%) was obtained in two crops on recrystallisation of the crude product from ethanol mp 260°-2°.

(b) Sodium 6,7,8,9-tetrahydro-5-hydroxy-4-oxo-10-propyl-4H-naphtho[2,3-b]pyran-2-carboxylate The product of step (a) (1.4 g) was suspended in water (20 ml) and sodium bicarbonate (356 mg) was added over 10 minutes. When homogeneity had been achieved the mixture was freeze-dried to yield a yellow solid which was shown to be a pure sample of the desired sodium salt (1.4 g; 93%).

EXAMPLE 9

6,7,8,9-Tetrahydro-5-hydroxy-4-oxo-10-propyl-4H-naphtho[2,3-b]pyran-2-carboxylic acid (a) Ethyl 6,7,8,9-tetrahydro-5-hydroxy-4-oxo-10-propyl-4H-naphtho[2,3-b]pyran-2-carboxylate A solution of the product of Example 6(a) (13.5 g) in concentrated sulphuric acid (120 ml) was stirred at 8° while a solution of sodium nitrite (3.4 g) in water (7 ml) was added dropwise. The solution was then stirred at 8° for 30 minutes, poured slowly into 50% v/v sulphuric acid (200 ml) at 115°-125° and the temperature of the resulting mixture maintained for 30 minutes. The mixture was then partly cooled and added to water (300 ml) with stirring. The precipitated solid was filtered off and recrystallised from ethanol. The solid obtained as dried, suspended in a mixture of ethanol (150 ml) and concentrated sulphuric acid (2 ml) and refluxed with stirring for 20 hours. The mixture was concentrated and cooled. The precipitated solid was filtered off, recrystallised from ethanol and dried to give ethyl 6,7,8,9-tetrahydro-5-hydroxy-4-oxo-10-propyl-4H-naphtho[2,3-b]pyran-2-carboxylate (4.5 g) mp 136°-133°.

(b) 6,7,8,9-Tetrahydro-5-hydroxy-4-oxo-10-propyl-4H-naphtho[2,3-b]pyran-2-carboxylic acid A refluxing solution of ethyl 6,7,8,9-tetrahydro-5-hydroxy-4-oxo-10-propyl-4H-naphtho[2,3-b]pyran-2-carboxylate (45.4 g) in ethanol (600 ml) was stirred whilst adding a solution of sodium bicarbonate (11.5 g) in water (300 ml) over 15 minutes. After refluxing a further 4 hours, an additional quantity of sodium bicarbonate solution (1.5 g in 30 ml water) was added and the mixture refluxed for a further 1 hour. The hot solution was acidified with dilute hydrochloric acid and the yellow precipitate filtered off. The damp solid was recrystallised from acetone to give 6,7,8,9-tetrahydro-5-hydroxy-4-oxo-10-propyl-4H-naphtho[2,3-b]pyran-2-carboxylic acid (31.0 g) mp 265°-268°.

EXAMPLE 10

(a) 5-Chloro-6,7,8,9-tetrahydro-4-oxo-10-propyl-4H-naphtho[2,3-b]pyran-2-carboxylic acid Ethyl 5-amino-6,7,8,9-tetrahydro4-oxo-10-propyl-4H-naphtho[2,3-b]pyran-2-carboxylate (7.2 g) in concentrated hydrochloric acid (80 ml) was treated with sodium nitrite (1.8 g) in water (15 ml) with stirring at 0° over 15 minutes.

The resulting diazonium salt-suspension/solution was added to a stirred solution of cuprous chloride (freshly prepared by standard techniques from 9 g of cupric sulphate) at 0°. The mixture was gradually heated to 120° over 90 minutes, and then allowed to cool to room temperature.

The resulting sand-coloured solid was filtered off and washed with water. The solid was dissolved in saturated sodium bicarbonate solution and heated on a steam bath for 30 minutes. The solution was acidified (HCl) and the precipitate was filtered off (4.9 g) and recrystallised twice from ethanol and then twice from acetic acid to give the title compound (2.6 g; 37.6%) mp 269°-71°.

(b) Sodium 5-chloro-6,7,8,9-tetrahydro-4-oxo-10-propyl-4H-naphtho[2,3-b]pyran-2-carboxylate The product of step (a) (2.27 g) suspended in water (15 ml) was treated with sodium bicarbonate (0.591 g). The resulting solution was filtered and reduced to a 10 ml bulk on the rotary evaporator. Acetone (70 ml) was added causing crystallisation to occur. A pale yellow solid (1.15 g; 47.4%) was obtained in two crops, which were blended and shown to be pure sodium salt.

EXAMPLE 11

(a) 10-Allyl-6,7,8,9-tetrahydro-4-oxo-4H-naphtho[2,3-b]-pyran-2-carboxylic acid The product of Example 3(a) (6.6 g) and sodium bicarbonate (1.78 g) were heated under reflux for 1 hour in a mixture of water (100 ml) and methanol (50 ml). The hot solution was filtered and the filtrate was evaporated to yield a white solid, which was taken up in water. The resulting solution was acidified with concentrated hydrochloric acid and the white solid was filtered off and washed well with cold water. On drying in a vacuum oven, an off-white powder of moderately pure title compound m.p. 235°–7° (6.0 g; 100%) was obtained. A pure sample of the compound was obtained as cream-coloured crystals after two recrystallisations from ethanol. Yield (4.7 g; 79%) m.p. 238°–240°.

(b) Sodium 10-allyl-6,7,8,9-tetrahydro-4-oxo-4H-naphtho[2,3-b]pyran-2-carboxylic The product of step (a) (3.0 g) was converted into its sodium salt (2.9 g) by the method of Example 4(d).

EXAMPLE 12

6,7,8,9-Tetrahydro-4-oxo-10-propyl-4H-naphtho8 2,3-b]pyran-2-carboxylic acid The product of Example 11(a) (6.2 g) was hydrogenated at 15 psi for 2½ hours at room temperature after which time hydrogen ceased to be absorbed. The fawn-coloured solid so obtained (6.0 g; 97%) was recrystallised from ethanol to give an analytically pure fawn solid m.p. 245°–5° (decomp), (5.2 g; 72%), identical to that obtained by the method of Example 1(f).

EXAMPLE 13

5-Dimethylamino-6,7,8,9-tetrahydro-4-oxo-10-propyl-4H-naphtho[2,3-b]pyran-2-carboxylic acid

(a) Ethyl 5-dimethylamino-6,7,8,9-tetrahydro-4-oxo-10-propyl-4H-naphtho[2,3-b]pyran-2-carboxylate The product of Example 6(a) (1.65 g) was dissolved in calcium chloride dried methylene chloride (15 ml) at −20°, and methoxysulphonylfluoride (1.14 g=0.86 ml) was added with stirring. The mixture was stirred at −20° for 1 hour, then at room temperature for 3 hours, at which time a further aliquot of methoxy sulphonyl fluoride (0.25 ml) was added. Stirring was continued at room temperature overnight. The reaction mixture was washed with water (100 ml), saturated aqueous sodium bicarbonate (2×100 ml), water (100 ml) and dried (anhydrous sodium sulphate) to yield a brown oil which was boiled with petroleum ether (60°–50°), filtered and the filtrate evaporated to give a brown oil which crystallised to a brown solid (1.3 g; 73%). This solid was a pure sample of ethyl 5-dimethylamino-6,7,8,9-tetrahydro-4-oxo-10-propyl-4H-naphtho[2,3-b]pyran-2-carboxylate mp 61°–62.5°.

(b) 5-Dimethylamino-6,7,8,9-tetrahydro-4-oxo-10-propyl-4H-naphtho[2,3-b]pyran-2-carboxylic acid hydrochloride The product of step (a) (1.8 g), sodium bicarbonate (0.5 g), water (20 ml), and ethanol (12 ml) were heated under reflux for 3 hours. The ethanol was removed on the rotary evaporator and the resulting solution was acidified (to pH 4). The resulting solution was then evaporated to a volume of 10 ml, causing crystallisation of the (approximately) hemihydrochloride. The buff solid was filtered off and combined with a similar solid obtained from a larger scale (6.0 g) hydrolysis of the starting ester. The combined solids were dissolved in 50% (vol/vol) hydrochloric acid (25 ml), evaporated and dried to yield after recrystallisation from water, the desired hydrochloride (3.6 g; 50%) mp 209° (decomp).

EXAMPLE 14

5-Ethylamino-6,7,8,9-tetrahydro-4-oxo-10-propyl-4H-naphtho[2,3-b]pyran-2-carboxylic acid

(a) Ethyl 5-ethylamino-6,7,8,9-tetrahydro-4-oxo-10-propyl-4H-naphtho[2,3-b]pyran-2-carboxylate Triethyloxonium borofluoride (2.7 g) in calcium chloride dried methylene chloride (25 ml) was added dropwise to a solution of the product of Example 6(a) (4.7 g) in methylene chloride (15 ml) over 15 minutes, with stirring, at 0°. The mixture was allowed to attain ambient temperature, then it was stirred for 2.5 hours. It was then poured into water and washed wtith water (50 ml), saturated aqueous sodium bicarbonate (2×50 ml), water (50 ml) and dried (anhydrous sodium sulphate) to yield a brown oil which crystallised from petroleum ether (60°–80°) as brown needles (3.6 g; 71%). This solid (1.0 g) was recrystallised from petroleum ether (60°–80°) to yield an analytically pure sample (600 mg; 60% recovery) of ethyl 5-ethylamino-6,7,8,9-tetrahydro-4-oxo-10-propyl-4H-naphtho[2,3-b]pyran-2-carboxylate as brown needles mp 91.5°.

(b) 5-Ethylamino-6,7,8,9-tetrahydro-4-oxo-10-propyl-naphtho[2,3-b]pyran-2-carboxylic acid The product of step (a) (1.2 g), sodium bicarbonate (310 mg), water (15 ml) and ethanol (15 ml) were heated under reflux for 80 minutes. The ethanol was removed on the rotary evaporator and the solution was acidified (with concentrated HCl) to pH 1. The brown solid was filtered off and combined with a similar solid obtained from a larger scale (4.8 g) by hydrolysis of the ester. The combined solids were recrystallised from ethanol to give a pure sample of the title compound (4.2 g; 77%) mp 213°–16°.

EXAMPLE 15

(a) 4-Oxo-10-propyl-4H-naphtho[2,3-b]pyran-2-carboxylic acid

The product of Example 1(d) (10 g) and sulphur (3 g) were heated at 230°–245° for 2 hours. A further quantity (0.5 g) of sulphur was added and heating was continued between 265° and 250° for 1 hour. The product was dissolved in ethanol and treated with decolourising charcoal. A dark brown solid crystallised from the filtered and cooled ethanol solution. Recrystallisation (three times) from ethanol gave a moderately pure sample of ethyl 4-oxo-10-propyl-4H-naphtho[2,3-b]pyran-2-carboxylate as pale brown needles (3.9 g; 39.6%). This solid (3.9 g) was heated under reflux with sodium bicarbonate (1.5 g), water (100 ml) and ethanol (50 ml) for 2 hours. The ethanol was removed on the rotary evaporator and the resulting solution was acidified (with concentrated HCl) to yield a brown solid which was recrystallised twice from chloroform, then twice from acetone to yield a nearly pure sample of the title acid (0.7 g; 20%) as light brown needles mp 265°–7°.

(b) Sodium 4-oxo-10-propyl-4H-naphtho[2,3-b]pyran-2-carboxylate

The product of step (a) (0.6 g) was converted into its corresponding sodium salt (0.55 g) by the method of Example 4(d).

EXAMPLE 16

5-Fluoro-6,7,8,9-tetrahydro-4-oxo-10-propyl-4H-naphtho[2,3-b]pyran-2-carboxylic acid (a) Ethyl 5-diazoniumhexafluorophosphate-6,7,8,9-tetrahydro-4-oxo-10-propyl-4H-naphtho[2,3-b]pyran-2-carboxylate Ethyl 5-amino-6,7,8,9-tetrahydro-4-oxo-10-propyl-4H-naphtho[2,3-b]pyran-2-carboxylate (20 g) was suspended in concentrated HCl (40 ml) at 5° and a solution of sodium nitrite (5.0 g) in water (20 ml) was added dropwise over 30 minutes maintaining the temperature between 5° and 10°. Hexafluorophosphoric acid (10 g of a 65% aqueous solution=15 ml) was added, causing a sticky solid to precipitate. The aqueous solution was decanted and the residue was triturated with methanol/ether to give a fawn solid, which was filtered off and washed with aliquots of water, methanol and ether, to yield a pale fawn solid (8.1 g; 31%) of ethyl 5-diazoniumhexafluorophosphate-6,7,8,9-tetrahydro-4-oxo-10-propyl-4H-naphtho[2,3-b]pyran-2-carboxylate mp 120°–1° (decomp). A further 6.4 g, 25% of this compound was recovered from the washings. Total yield 14.5 g (56%).

(b) Ethyl 5-fluoro-6,7,8,9-tetrahydro-4-oxo-10-propyl-4H-naphtho[2,3-b]pyran-2-carboxylate The product of step (a) (14.5 g) was heated at 125°–140° for several minutes until nitrogen evolution had ceased. The black solid (10.8 g) was purified by column chromatography (on silica). Toluene/ethyl acetate eluted a pale yellow solid (2.5 g; 23%) of moderately pure ethyl ester mp 126°–129°. Two recrystallisations from cyclohexane gave the required product (1.8 g), mp 132°–4°.

(c) 5-Fluoro-6,7,8,9-tetrahydro-4-oxo-10-propyl-4H-naphtho[2,3-b]pyran-2-carboxylic acid The ester of step (b) (2.40 g) was converted into the corresponding acid (1.5 g; 66%), mp 249°–253°, by the method of Example 5(b).

(d) Sodium 5-fluoro-6,7,8,9-tetrahydro-4-oxo-10-propyl-4H-naphtho[2,3-b]pyran-2-carboxylate The product of step (c) (1.0 g) was converted into its sodium salt (0.85 g) by the method of Example 4(d).

EXAMPLE 17

(a) 6,7,8,9-Tetrahydro-4-oxo-10-(2-hydroxypropyl)-4H-naphtho[2,3-b]pyran-2-carboxylic acid The product of Example 11(b) (12.0 g) was dissolved in water (800 ml) and mercuric acetate (12.5 g) was added. This mixture was stirred and heated on a steam bath overnight. Sodium bicarbonate (3.3 g) sodium chloride (30 gm) and dioxan (750 ml) were added and heating was continued until solution was complete. Sodium borohydride (3.0 g) was added and mercury was precipitated. The mixture was acidified to pH 7 and the mercury was removed by decantation. Acidification of the filtrate was continued to pH 1 and the solution was evaporated to small bulk giving a solid which was filtered off. This solid was washed well with hot ethyl acetate and the solid which remained undissolved, being required compound, was collected and dried (2.5 g, 21%) mp 235°.

(b) Sodium 6,7,8,9-tetrahydro-4l-oxo-10-(2-hydroxypropyl)-4H-naphtho[2,3-b]pyran-2-carboxylate To a solution of sodium bicarbonate (0.668 g) in water (20 ml) was added the product of step (a) (2.401 g) and the resulting solution was freeze-dried. The white deliquescent solid obtained was crystallised from ethanol to give the desired sodium salt (1.6 g, 62%).

EXAMPLE 18

(a) 7,8,9,10-Tetrahydro-5-hydroxy-4-oxo-6-propyl-4H-naphtho[1,2-b]pyran-2-carboxylic acid The product of Example 9(a) (6.6 g) was heated with aqueous sodium bicarbonate (4.0 g) in water (50 ml) and ethanol (5 ml) at reflux for 24 hours. The resulting solution was evaporated to small volume and allowed to cool. The solid deposited was filtered off, dissolved in water and the aqueous solution was acidified to give the title compound (4.4 gm, 66%), mp 226°–7°.

(b) Sodium 7,8,9,10-tetrahydro-5-hydroxy-4-oxo-6-propyl-4H-naphtho[1,2-b]pyran-2-carboxylate The product of step (a) (4.316 g) was dissolved in a hot solution of sodium bicarbonate (1.21 g) in water (50 ml) and the resulting solution was cooled at 5° overnight. The solid which crystallised was filtered off and dried to give the desired sodium salt as a yellow solid (4.2 g, 90%).

EXAMPLE 19

10-Bromo-6,7,8,9-tetrahydro-4-oxo-4H-naphtho[2,3-b]pyran-2-carboxylic acid (a) 7-Acetyl-5-bromo-1,2,3-tetrahydro-6-hydroxynaphthalene A mixture of aluminium chloride (8.15 g) and 7-acetyl-1,2,3,4-tetrahydro-6-hydroxynaphthalene (4.75 g) in dichloromethane (250 ml) was cooled to −10°. A solution of bromine (6.0 g) in dichloromethane (150 ml) was then added over 1 hour with constant stirring. The reaction mixture was allowed to warm to room temperature overnight, dilute HCl (400 ml) was added and the organic layer was separated, washed with water and dried (MgSO$_4$). The solvent was filtered and the filtrate was evaporated to dryness leaving an oil which solidified on coolig to give 7-acetyl-5-bromo-1,2,3,4-tetrahydro-6-hydroxynaphthalene (5.3 g, 79%) mp 127°–130°.

(b) Ethyl 10-bromo-6,7,8,9-tetrahydro-1-oxo-4H-naphtho[2,3-b]pyran-2-carboxylate The product of step (a) (5.3 g) was treated with sodium (2.3 g) and diethyl oxalate (7.3 g) under the conditions of Example 1(d) to give the title ester (5.0 g; 72%), mp 130°–132°.

(c) 10-Bromo-6,7,8,9-tetrahydro-4-oxo-4H-naphtho[2,3-b]pyran-2-carboxylic acid

The ester product of step (b) (4.2 g) was converted into the corresponding carboxylic acid (3.2 g; 83%), mp 188°–191°, by the method of Example 5(b).

(d) Sodium 10-bromo-6,7,8,9-tetrahydro-4-oxo-4H-naphtho[2,3-b]pyran-2-carboxylate The acid product of step (c) (2.8 g) was converted into the corresponding sodium salt (2.7 g; 89%), by the method of Example 4(d).

EXAMPLE 20

6,7,8,9-Tetrahydro-5-methoxy-4-oxo-10-propyl-4H-naphtho[2,3-b]pyran-2-carboxylic acid (a) Methyl 6,7,8,9-tetrahydro-5-hydroxy-4-oxo-10-propyl-4H-naphtho[2,3-b]pyran-2-carboxylate A mixture of the product of Example 8(a) (34.4 g), methanol (1000 ml) and concentrated sulphuric acid (5 ml) was heated to reflux temperature and a homogeneous solution was obtained. Refluxing was continued for a further 18 hours. The solution was then allowed to cool and the methanol was evaporated in vacuo to give a brown solid. This solid was dissolved in acetone and the solution was treated with charcoal. Filtering off the charcoal and evaporation of the acetone gave a yellow solid which was recrystallised from methanol to give methyl 6,7,8,9-tetrahydro-5-hydroxy-4-oxo-10-propyl-4H-naphtho[2,3-b]pyran-2-carboxylate (20.6 g).

(b) Methyl 6,7,8,9-tetrahydro-5-methoxy-4-oxo-10-propyl-4H-naphtho[2,3-b]pyran-2-carboxylate To a solution of the product of step (a) (20.6 g) in dry acetone (1000 ml) was added powdered anhydrous potassium carbonate (9.91 g) and methyl iodide (20.3 ml) and the stirred reaction mixture was refluxed gently. Further quantities of the reagents were added as follows:
at 24 hours, methyl iodide, (20.3 ml),
at 48 hours, methyl iodide, (20.3 ml),
at 96 hours, potassium carbonate (4.5 g).

After refluxing for 118 hours the reaction mixture was allowed to cool, the potassium carbonate was filtered off and the acetone was removed by evaporation in vacuo. The resulting yellow solid was dissolved in ether and the ethereal solution was washed with water. The organic solution was then dried (magnesium sulphate) and filtered, and the ether was evaporated in vacuo. The crude product was recrystallised twice from petroleum ether (60°–80°) to give methyl 6,7,8,9-tetrahydro-5-methoxy-4-oxo-10-propyl-4H-naphtho[2,3-b]pyran-2-carboxylate as a fawn solid (13.8 g), mp 92°–93°.

(c) 6,7,8,9-Tetrahydro-5-methoxy-4-oxo-10-propyl-4H-naphtho[2,3-b]pyran-2-carboxylic acid The product of step (b) (2 g) was hydrolysed to the corresponding acid (1.55 g), mp 228°–229°, by the method of Example 5(b).

(d) Sodium 6,7,8,9-tetrahydro-5-ethoxy-4-oxo-10-propyl-4H-naphtho[2,3-b]pyran-2-carboxylate The acidic product of step (c) (1.1 g) was converted into its sodium salt (1.0 g), by the method of Example 4(d).

EXAMPLE 21

6,7,8,9-Tetrahydro-3-methyl-4-oxo-10-propyl-4H-naphtho[2,3-b]pyran-2-carboxylic acid (a) 5,6,7,8-Tetrahydro-2-propionoxynaphthalene To a stirred solution of 5,6,7,8-tetrahydro-2-hydroxy naphthalene (44.5 g) in dry pyridine (200 ml) was added propionic anhydride (45.6 g). The mixture was heated on a steam bath for 2 hours, left overnight, then poured into stirred 5 N hydrochloric acid and extracted with chloroform. The chloroform extract was washed with N HCl, with water, dried (MgSO$_4$), filtered and evaporated to leave the title product, (61 g) as a pale brown oil.

(b) 5,6,7,8-Tetrahydro-2-hydroxy-3-propionylnaphthalene

To a mixture of aluminium chloride (120 g) and sodium chloride (52.6 g) at 160° was added, over 10 minutes, the product of step (a) (60 g). The mixture was then heated at 180° for 30 minutes, cooled and poured onto ice. The precipitate was extracted into ether and the extract was filtered and evaporated. The residue was twice crystallised from petroleum ether (40°–60°) to give 5,6,7,8-tetrahydro-2-hydroxy-3-propionylnaphthalene, (14.5 g) as a pale brown solid, m.p 57°–58°.

(c) 2-Allyloxy-5,6,7,8-tetrahydro-3-propionylnaphthalene

The product of step (b) (14.5 g) was treated with allyl bromide (11.5 g) under the conditions of Example 1(a) to give the title compound (18.8 g) as a pale brown oil, whose structure was confirmed by MS and NR spectroscopy.

(d) 1-Allyl-5,6,7,8-tetrahydro-2-hydroxy-3-propionylnaphthalene

The product of step (c) (18 g) was thermally rearranged to the title compound (17 g), by the method of Example 1(b).

(c) Ethyl 10-allyl-6,7,8,9-tetrahydro-3-methyl-4-oxo-4H-naphtho[2,3-b]pyran-2-carboxylate The product of step (d) (17 g) was treated with sodium (8 g) and diethyl oxalate (25.5 g) under the conditions of Example 1(d) to give the title ester (16 g) as a pale brown oil, which was characterised by NR spectroscopy.

(f) Ethyl 6,7,8,9-tetrahydro-3-methyl-4-oxo-10-propyl-4H-naphtho[2,3-b]pyran-2-carboxylate The product of step (e) (16 g) was hydrogenated over palladium on charcoal catalyst, under the conditions of Example 3(b), to give the title ester (16.2 g), as a low melting brown solid.

(g) 6,7,8,9-Tetrahydro-3-methyl-4-oxo-10-propyl-4H-naphtho[2,3-b]pyran-2-carboxylic acid A mixture of the product of step (f) (16.2 g), glacial acetic acid (80 ml) and 5 N hydrochloric acid (20 ml) was heated and stirred on a steam bath overnight, and then evaporated. The residue was extracted with aqueous sodium bicarbonate and the extract was filtered and then acidified. Precipitated material was isolated by decantation and was triturated with water, dried, then triturated with an ether/petroleum ether (40°–60°) mixture. There remained as an insoluble off-white solid, 6,7,8,9-tetrahydro-3-methyl-4-oxo-10-propyl-4H-naphtho[2,3-b]pyran-2-carboxylic acid, (3.5 g), m.p 162°–4°.

(h) Sodium 6,7,8,9-tetrahydro-3-methyl-4-oxo-10-propyl-4H-naphtho[2,3-b]pyran-2-carboxylate A solution of sodium bicarbonate (0.78 g) in water (30 ml) was added to the product of step (g) (2.8 g). The resulting solution was filtered then evaporated to small volume and diluted with acetone. Crystallisation occurred and the resulting crystals were filtered off and recovered as an off-white solid, which was the desired sodium salt (2.65 g).

EXAMPLE 22

7,8-Dihydro-4-oxo-10-propyl-4H,6H-benzo[1,2-bis,4-b']dipyran-2-carboxylic acid (a) 6-Acetyl-2,3-dihydro-7-allyloxy-4H(l)benzopyran 6-Acetyl-2,3-dihydro-7-hydroxy-4H(l) benzopyran (20 g) was treated with allyl bromide (12.1 ml), under the conditions of Example 1(a), to give the title compound (23.9 g: 99%), mp 62°–64°.

(b) 6-Acetyl-2,3-dihydro-7-hydroxy-S-allyl-4H(l) benzopyran

The allyl ether of step (a) (23.9 g) was heated at 200°–210° for 1.25 hours. The reaction mixture was cooled, diluted with water and extracted with ether. The ethereal extract was washed with water, dried and the solvent evaporated to give 23.3 g of the product, mp 67°–71° (97.5%).

(c) 6-Acetyl-2,3-dihydro-7-hydroxy-8-propyl-4H(l) benzopyran

The compound from step (b) (19 g) was dissolved in ethanol (200 ml) and hydrogenated in the presence of 5% palladium on charcoal (1.0 g) at 45 psi until hydrogen uptake had ceased. The catalyst was filtered off and the filtrate evaporated to give 9.6 g of the desired product mp 62°–66° (95.2%).

(d) Ethyl 7,8-dihydro-4-oxo-10-propyl-4H,6H-benzo[1,2-b:5,4-b']dipyran-2-carboxylate The product of step (c) (9.6 g) was treated with sodium (4.71 g) and diethyl oxalate (15.0 g), under the conditions of Example 1(d), to give the title ester (10.7 g:82.6%), mp 100°–103°.

(e) 7,8-Dihydro-4-oxo-10-propyl-4H,6H-benzo[1,2-b:5,4-b']dipyran-2-carboxylic acid The ester from step (d) (8.6 g) was hydrolysed to the corresponding acid (5.9 g) mp 261°–262° (decomp), using the conditions of Example 5(b).

(f) Sodium 7,8-dihydro-4-oxo-10-propyl-4H,6H-benzo[1,2-b:5,4-b']dipyran-2-carboxylate The acid of step (c) (4.61 g) was added to sodium bicarbonate (1.354 g), in water (200 ml). The solution was filtered and the filtrate was freeze-dried to give 4.15 g of the sodium salt which analysed as a dihydrate.

EXAMPLE 23

5-Allyloxy-6,7,8,9-tetrahydro-4-oxo-10-propyl-4H-naphtho[2,3-b]pyran-2-carboxylic acid A stirred solution of the product of Example 8(a) (1.5 g) in dimethylformamide (15 ml) was treated with a 50% w/w oil dispersion of sodium hydride (0.5 g). This mixture was slightly warmed and the resulting suspension was treated with a solution of allyl bromide (7 g) in dimethylformamide (10 ml). After stirring at room temperature for 10 minutes the mixture was heated under reflux for 5 minutes then evaporated. The residue was treated with water (30 ml), methanol (10 ml) and sodium bicarbonate (0.8 g) and heated under reflux for 1.5 hours. The mixture was evaporated, diluted with water and the aqueous solution was filtered then acidified with hydrochloric acid. Precipitated material was triturated with water, dried and the title compound recovered as a yellow powder (1.4 g) mp 162°–8° (molecular weight 342, structure confirmed by Mass Spectroscopy).

EXAMPLE 24

(a) 6,7,8,9-Tetrahydro-4-oxo-5-propoxy-10-propyl-4H-naphtho[2,3-b]pyran-2-carboxylic acid A solution of the product of Example 23 (1.4 g) in ethanol (25 ml) was treated with a 5% palladium on charcoal catalyst (50 mg) and hydrogenated at 45 psi/room temperature for 5 hours. Catalyst was filtered off and the ethanolic filtrate was evaporated to low bulk, treated with sodium bicarbonate (0.8 g) and water (30 ml), and heated under reflux for 1 hour. The solution was evaporated, diluted with water and filtered and the filtrate was acidified. The precipitated acid was filtered off, washed with water, dried and the title compound recovered as a pale yellow powder (1.4 g), mp 203° (decomp).

(b) Sodium
6,7,8,9-tetrahydro-4-oxo-5-propoxy-10-propyl-4H-naphtho[2,3-b]pyran-2-carboxylate An aqueous solution of sodium bicarbonate (0.35 g) and the product of step (a) (1.35 g) was filtered, evaporated to near dryness then diluted with acetone. Crystallisation occurred and the crystals were filtered off and the desired sodium salt recovered as a cream powder (1.2 g).

EXAMPLE 25

Sodium
8,9-dihydro-5-ethoxy-8,8-dimethyl-4-oxo-4H,10H-benzo[1,2-b: 3,4-b']dipyran-2-carboxylate (a) 5-Hydroxy-7-methoxy-2,2-dimethylchroman was prepared according to literature procedures.

(b)
8,9-Dihydro-5-methoxy-8,8-dimethyl-4-oxo-4H,10H-benzo[1,2-b: 3,4-b']dipyran-2-carboxylic acid To a solution of dimethylacetylenedicarboxylate (7.5 g) in dioxan (100 ml) containing 'Triton 8' (10 drops) was added 5-hydroxy-7-methoxy-2,2-dimethylchroman (10.0 g) and the resulting mixture was warmed on a steam bath for 2 hours. A solution of sodium hydroxide (4.0 g) in water (20 ml) was added and heating was continued for 2 hours more. The organic solvent was removed and water (50 ml) was added to the residue and the mixture was acidified to give an oil which was extracted into ethylacetate. This solution was dried over MgSO$_4$, filtered and the filtrate was evaporated to dryness. The oil so obtained was dissolved in concentrated H$_2$SO$_4$ (50 ml) and the solution was stirred at room temperature for 30 minutes, poured into ice and extracted with ethyl acetate. This solution was washed with water, dried (MgSO$_4$), filtered and evaporated to dryness. The oil so produced was triturated with ethyl acetate, cooled to 0°, and the solid produced was filtered and dried. The solid was crystallised from ethanol to give 8,9-dihydro-5-methoxy-8,8-dimethyl-4-oxo-4H,10H-benzo[1,2-b: 3,4-b']dipyran-2-carboxylic acid as a white solid (3.4 g, 23%) mp 225°-6°.

(c) Sodium
8,9-dihydro-5-methoxy-8,8-dimethyl-4-oxo-4H,10H-benzo[1,2-b: 3,4-b']dipyran-2-carboxylate The acidic product of step (b) (1.4 g) was converted into its sodium salt (1.3 g: 87%), by the method of Example 4(d).

EXAMPLE 26

(a) Ethyl
2,3,6,7,8,9-hexahydro-2-hydroxy-4-oxo-10-propyl-4H-naphtho[2,3-b]pyran-2-carboxylate A solution of the product of Example 1(c) (5.75 g) and diethyl oxalate (7.3 g) in petroleum ether (60°-80°) (50 ml), was treated with a 50% w/w dispersion of sodium hydride in oil (2.5 g). The mixture was stirred and gently heated until all of the hydride had reacted. To the mixture was then added ethanol (25 ml) and concentrated hydrochloric acid (5 ml). This mixture was heated under reflux for 5 minutes, cooled and evaporated. The residue was treated with a water/chloroform mixture and the chloroform layer was isolated, washed with water and evaporated. This residue was crystallised from an ethyl acetate/petroleum ether (60°-80°) mixture to give ethyl 2,3,6,7,8,9-hexahydro-2-hydroxy-4-oxo-10-propyl-4H-naphtho[2,3-b]pyran-2-carboxylate as white crystals, (4.3 g), mp 126°-8°. (The structure was confirmed by NMR spectroscopy).

(b) Ethyl
6,7,8,9-tetrahydro-4-oxo-10-propyl-4H-naphtho[2,3-b]pyran-2-carboxylate The product of step (a) (1 g) in ethanol (50 ml) containing concentrated HCl (1 ml) was heated under reflux for 4 hours. Evaporation of the resulting solution to a volume of 20 mls caused the chromone ester, identical to that of Example 1(d) to crystallise.

EXAMPLE 27

Methyl
7,8,9,10-tetrahydro-5-methoxy-4-oxo-6-propyl-4H-naphtho[1,2-b]pyran-2-carboxylate (a) Methyl
7,8,9,10-tetrahydro-5-hydroxy-4-oxo-6-propyl-4H-naphtho[1,2-b]pyran-2-carboxylate The product of Example 18(a) (1.0 g) was converted into the corresponding methyl ester (0.8 g), mp 153°-154° by the method of Example 20(a).

(b) Methyl
7,8,9,10-tetrahydro-5-methoxy-4-oxo-6-propyl-4H-naphtho[1,2-b]pyran-2-carboxylate The product of step (a) (0.5 g) was converted into the title compound (0.2 g) mp 124°, by the method of Example 20(b). The product of step (b) may be hydrolysed to the free acid.

EXAMPLE 28

5-Hydroxy-4-oxo-10-propyl-4H-naphtho[2,3-b]pyran-2-carboxylic acid (a) Ethyl
1-hydroxy-4-oxo-10-propyl-4H-naphtho[2,3-b]pyran-2-carboxylate The product of Example 9(a) (10 g) and sulphur (1.5 g) were ground together to form an intimate mixture. This was heated at 250° under an atmosphere of nitrogen for one and a half hours. After cooling to room temperature the reaction mixture was extracted with acetone, removal of the acetone in vacuo yielded a dark brown amorphous material. This was crystallised from acetone/ethyl acetate with charcoaling, to yield the desired product as dark orange needles, mp 148°-150°, 3.4 g (35%).

(b) Sodium
5-hydroxy-4-oxo-10-propyl-4H-naphtho[2,3-b]pyran-2-carboxylate

The product of step (a) (6 g) was heated at 100° with sodium bicarbonate (1.55 g) in a mixture of water (50 ml) and ethanol (5 ml), for 4 hours. The ethanol was removed, in vacuo, and the remaining aqueous solution was filtered and cooled. The sodium salt (1.8 g) crystallised from this solution as orange needles.

(c)
5-Hydroxy-4-oxo-10-propyl-4H-naphtho[2,3-b]pyran-2-carboxylic acid

The product of step (b) (0.2 g) was dissolved in hot water (20 ml) and acidified with hydrochloric acid. The title acid precipitated as an orange solid (0.18 g) mp 283° (decomp).

EXAMPLE 29

10-Formyl-6,7,8,9-tetrahydro-4-oxo-4H-naphtho[2,3-b]pyran-2-carboxylic acid (a) 5,6,7,8-Tetrahydro-3-acetyl-1-formyl-2-naphthol To a solution of 5,6,7,8-tetrahydro-3-acetyl-2-naphthol (9.5 g) in dry dichloromethane (50 ml), cooled in an ice bath, was added titanium tetrachloride (38 g) over a period of three minutes. After fifteen minutes stirring dichloromethyl methyl ether (8.05 g) was added over a period of five minutes. The mixture was retained in the ice bath for a further ten minutes, then stirred without cooling for thirty minutes, and finally warmed to 35° for twenty minutes.

The reaction mixture was thrown into ice-water (250 ml), stirred for five minutes, and the organic phase was separated. The aqueous phase was extracted into dichloromethane (3×75 ml). After drying, the combined organic phases were evaporated to yield a red-orange solid (10.5 gm, 95%) which was pure enough for subsequent reactions.

Crystallisation of a small sample from ethanol gave the title product as red-orange needles, mp 77.5°–78.5°.

(b) Ethyl 10-formyl-6,7,8,9-tetrahydro-4-oxo-4H-naphtho[2,3-b]pyran-2-carboxylate The product of step (a) (5.5 g) was treated with sodium (1.45 g) and diethyl oxalate (18.25 g), under the conditions described in Example 1(d), to give the title ester (7.7 g), mp 134°–135°, as yellow needles.

(c) 10-Formyl-6,7,8,9-tetrahydro-4-oxo-4H-naphtho[2,3-b]pyran-2-carboxylic acid

The product of step (b) (6.0 g) was hydrolysed to the corresponding acid using the conditions of Example 5(b) m.p. 200°(decomp).

(d) Sodium 10-Formyl-6,7,8,9-tetrahydro-4-oxo-4H-naphtho[2,3-b]pyran-2-carboxylate The product of step (c) (3.0 g) was converted into its sodium salt (2.9 g), by the method of Example 4(d).

EXAMPLE 30

Ethyl 6,7,8,9-tetrahydro-10-ethoxyethyl-4-oxo-4H-naphtho[2,3-b]pyran-2-carboxylate (a) 7-Acetyl-1,2,3,4-tetrahydro-6-hydroxy-5-chloromethyl-naphthalene To a solution of 7-acetyl-1,2,3,4-tetrahydro-6-hydroxynaphthalene (100 g) in acetic acid (350 ml) was added paraformaldehyde (29 g), concentrated hydrochloric acid (500 ml) and orthophosphoric acid (150 ml). The resulting solution was heated on a steam bath for 2 hours, poured into water (3 l) and the oil which separated was extracted into ethyl acetate. This solution was washed with water, dried over MgSO4, filtered and evaporated to dryness leaving an oil. This was triturated with a small amount of ether and the yellow solid was filtered off and dried to give 7-acetyl-1,2,3,4-tetrahydro-6-hydroxy-5-chloromethylnaphthalene, 98 g (78%) mp 88°–90°.

(b) 7-Acetyl-1,2,3,4-tetrahydro-6-hydroxy-9-hydroxymethyl naphthalene

To a solution of the product of step (a) (23.8 g) in ethanol (500 ml) was added a solution of potassium hydroxide (11.2 g) in ethanol (250 ml) and water (100 ml). The resulting mixture was heated on a steam bath for 30 minutes, poured into water (2 l) and the mixture was made acid with concentrated hydrochloric acid. It was then extracted with ethyl acetate and the extracts were dried (MgSO4), filtered and the filtrate was evaporated to dryness leaving 7-acetyl-1,2,3,4-tetrahydro-6-hydroxy-9-hydroxymethylnaphthalene as an oil, 21 g (95%).

(c) Ethyl 10-ethoxymethyl-6,7,8,9-tetrahydro-4-oxo-4H-naphtho[2,3-b]pyran-2-carboxylate A solution of the product of step (b) (15.4 g) in ethanol (50 ml) was added to one of sodium (4.0 g) in ethanol (50 ml). To this mixture was added diethyl oxalate (50 g) and the whole mixture was heated at-reflux for 2 hours, then poured into a mixture of chloroform (500 ml) and concentrated HCl (100 ml). The organic layer was separated, evaporated to dryness and the residue was heated at reflux in ethanol (200 ml) containing concentrated hydrochloric acid (5 ml) for 2 hours. The solution was evaporated to dryness and the residue was taken up in ethyl acetate. This solution (was washed well with water, dried (MgSO4), filtered and the filtrate was evaporated to dryness leaving an oil. This was dissolved in a small amount of ethyl acetate and the solution was allowed to crystallise to give the title ester 6.3 g (30%), mp 115°–6°. It should be noted that under these reaction conditions the hydroxymethyl group of the starting naphthol has been converted into an ethoxymethyl grouping.

(d) 10-Ethoxymethyl-6,7,8,9-tetrahydro-4-oxo-4H-naphtho[2,3-b]pyran-2-carboxylic acid The product of step (c) (3.0 g) was hydrolysed to the corresponding acid mp 239° using the conditions of Example 5(b).

(e) Sodium 10-ethoxymethyl-6,7,8,9-tetrahydro-4-oxo-4H-naphtho[2,3-b]pyran-2-carboxylate The product of step (d) (2.1 g) was converted into its sodium salt-(2.0 g) by the method of Example 4(d).

EXAMPLE 31

6,7,8,9-Tetrahydro-10-(2,3-dihydroxyprop-1-yl)-4-oxo-4H-naphtho[2,3-b]pyran-2-carboxylic acid (a) Ethyl 10-(2,3-epoxyprop-1-yl)-6,7,8,9-tetrahydro-4-oxo-4H-naphtho[2,3-b]pyran-2-carboxylate A solution of the allyl compound of Example 3(a) (10 g) in dichloromethane (150 ml) was stirred at 0° while m-chloroperbenzoic acid (7.15 g) was added. The mixture was allowed to warm slowly to room temperature at which it was stirred for 2 days. The solution was washed with aqueous sodium metabisulphite, aqueous sodium bicarbonate and water and was dried (MgSO4).

The drying agent was removed by filtration and the filtrate was evaporated to dryness leaving a white solid which was crystallised from ethanol to give the required epoxide, 3.0 g (29%), mp 138°-140°.

(b) Ethyl 6,7,8,9-tetrahydro-10-(2,3-dihydroxyprop-1-yl)-4-oxo-4H-naphtho[2,3-b]pyran-2-carboxylate To a solution of the epoxide from step (a) (5.0 g) in dioxan (100 ml) was added water (20 ml) and concentrated sulphuric acid (0.5 ml). The resulting solution was heated on a steam bath for 30 minutes then poured into a large volume of water (1 l) and the mixture extracted with ethyl acetate. The extracts were washed well with water, dried (MgSO$_4$) and evaporated to small bulk. The title compound crystallised to give a yeild of 2.7 g (73%), mp 142°-4°.

(c) 6,7,8,9-Tetrahydro-10-(2,3-dihydroxyprop-1-yl)-4-oxo-4H-naphtho[2,3-b]pyran-2-carboxylic acid The ester product of step (b) (2.3 g) was hydrolysed to the title acid by the method of Example 5(b), mp 217°-218°.

(d) Sodium 6,7,8,9-tetrahydro-10-(2,3-dihydroxyprop-1-yl)-4-oxo-4H-naphtho[2,3-b]pyran-2-carboxylate The product of step (c) (1.6 g) was converted into its sodium salt (1.6 g), by the method of Example 4(d).

EXAMPLE 32

10-(3-Chloro-2-hydroxyprop-1-yl)-6,7,8,9-tetrahydro-4-oxo-4H-naphtho[2,3-b]pyran-2-carboxylic acid (a) 10-(3-Chloro-2-hydroxyprop-1-yl)-6,7,8,9-tetrahydro-4-oxo-4H-naphtho[2,3-b]pyran-2-carboxylic acid To a solution of the ester of Example 31(a) (10.0 g) in glacial acetic acid (150 ml) was added concentrated hydrochloric acid (75 ml) and the mixture was heated on a steam bath for 5 hours. This solution was diluted with a large volume of water (1 l) and the resulting solid was filtered and dried. The solid was crystallised from ethyl acetate to give the title acid, 3.3 g (30%), mp 242°-4° (decomp).

(b) Sodium 10-(3-chloro-2-hydroxyprop-1-yl)-6,7,8,9-tetrahydro-4-oxo-4H-naphtho[2,3-b]pyran-2-carboxylate To a suspension of the acid from step (a) (1.474 g) in water (30 ml) was added sodium bicarbonate (0.368 g) and the resulting solution was freeze-dried. The solid obtained was dried in vacuo to give the required salt, 1.4 g (89%).

EXAMPLE 33

4-Oxo-10-propyl-6,7,8,9-tetrahydro-4H-naphtho[2,3-b]pyran-2-carboxylic acid

2-Methyl-4-oxo-10-propyl-6,7,8,9-tetrahydro-4H-naphtho[2,3-b]pyran (0.06 g) and selenium dioxide (0.44 g) were dissolved in 20% aqueous dioxan (30 ml) and the resulting solution heated under reflux for 4 days. The reaction mixture was filtered and evaporated to dryness in vacuo. The residue was dissolved in ethyl acetate (200 ml). The resulting solution was filtered and extracted with saturated aqueous sodium bicarbonate (2×100 ml). The bicarbonate extracts were bulked acidified with 2 N aqueous hydrochloric acid and the resulting precipitate extracted into ethyl acetate (2×100 ml). The ethyl acetate extracts were bulked, dried (Na$_2$SO$_4$) and evaporated leaving the title compound as a bright-yellow solid (0.18 g), mp 245°-8°.

EXAMPLE 34

Methyl 5-methoxy-4-oxo-10-propyl-6,7,8,9-tetrahydro-4H-naphtho[2,3-b]pyran-2-carboxylate A mixture of methyl 2,3-dihydro-5-methoxy-4-oxo-10-propyl-6,7,8,9-tetrahydro-4H-naphtho[2,3-b]pyran-2-carboxylate (3.4 g) and N-bromosuccinimide (1.78 g) was heated at reflux in carbon tetrachloride (150 ml) for 6 hours. The solution was cooled, washed with water, dried (Na$_2$SO$_4$) and evaporated. The residue was crystallised from petroleum ether (60°-80°) giving the title compound as a fawn solid, mp 92°-3°.

EXAMPLE 35

5-Hydroxy-4-oxo-10-propyl-6,7,8,9-tetrahydro-4H-naphtho[2,3-b]pyran-2-carboxylic acid 5-Hydroxy-4-oxo-10-propyl-6,7,8,9-tetrahydro-4H-naphtho[2,3-b]pyran-2-carbonitrile (1.0 g) was dissolved in a mixture of dioxan (20 ml) and dilute hydrochloric acid (20 ml) and heated under reflux for 24 hours. The dioxan was evaporated in vacuo and the residue extracted with chloroform (100 ml). The chloroform solution was extracted with saturated aqueous sodium bicarbonate (50 ml) and then the bicarbonate extract acidified with dilute hydrochloric acid. The resulting precipitate was filtered off, washed with water and dried giving the title compound as a light-yellow solid, mp 260°-2°.

EXAMPLE 36

5-Hydroxy-4-oxo-10-propyl-6,7,8,9-tetrahydro-4H-naphtho[2,3-b]pyran-2-carboxylic acid A suspension of 5-methoxy-4-oxo-10-propyl-6,7,8,9-tetrahydro-4H-naphtho[2,3-b]pyran-2-carboxylic acid (5 g) in 48% aqueous hydrobromic acid (130 ml) was heated under reflux for 7 hours. The reaction mixture was cooled and excess saturated aqueous sodium bicarbonate added. The resulting solution was filtered, the filtrate acidified with concentrated hydrochloric acid and then extracted with chloroform (100 ml). The chloroform solution was dried (Na$_2$SO$_4$) and evaporated leaving a residue which, when crystallised from acetone, gave the title compound as an orange crystalline solid mp 259°-260°.

EXAMPLE 37

10-(2-Hydroxypropyl)-4-oxo-6,7,8,9-tetrahydro-4H-naphtho[2,3-b]pyran-2-carboxylic acid To a stirred solution of sodium borohydride (0.4 g) in 0.02 N aqueous sodium hydroxide (30 ml) was added dropwise a solution of 4-oxo-10-(2-oxopropyl)-6,7,8,9-tetrahydro-4H-naphtho[2,3-b]pyran-2-carboxylic acid (2.3 g) in 0.02 N aqueous sodium hydroxide (100 ml). The resulting solution was stirred at ambient temperature for 20 hours, then cooled in ice and acidified with dilute hydrochloric acid. The precipitate was filtered washed with water and dried giving the title compound as a white solid, mp 235°.

EXAMPLE 38

4-Oxo-10-propyl-6,7,8,9-tetrahydro-4H-naphtho[2,3-b]pyran-2-carboxylic acid

A mixture of 10-propyl-6,7,8,9-tetrahydro-4-thioxo-4H-naphtho[2,3-b]pyran-2-carboxylic acid (0.025 g), methyl iodide (3 drops), acetone (10 ml) and water (4 drops) was stirred in the dark at ambient temperature for 2 days. Concentration of the reaction mixture in vacuo gave a brown solid which on crystallisation from acetone gave the title compound as a light-yellow solid, mp 245°–8°.

EXAMPLE 39

5-Methoxy-4-oxo-10-propyl-6,7,8,9-tetrahydro-4H-naphtho[2,3-b]pyran-2-carboxylic acid A solution of 5-methoxy-10-propyl-4-spiro-2'-(1',3'-dithiane)-6,7,8,9-tetrahydro-4H-naphtho[2,3-b]pyran-2-carboxylic acid (0.1 g) and periodic acid (0.1 g) in a mixture of acetone (15 ml) and water (5 ml) was stirred at ambient temperature for 2 hours. Removal of the acetone in vacuo produced a solid which was extracted into chloroform (100 ml). The chloroform was washed with water, dried ($Na_2SO_4$) and evaporated leaving a solid which, when crystallised from acetone, gave the title compound as a bright-yellow solid, mp 228°–9°.

EXAMPLE 40

4-Oxo-10-propyl-6,7,8,9-tetrahydro-4H-naphtho[2,3-b]pyran-2-carboxylic acid

To a refluxing solution of 4-oxo-10-(2-oxopropyl)-6,7,8,9-tetrahydro-4H-naphtho[2,3-b]pyran-2-carboxylic acid (3.1 g) in water (100 ml) containing sodium hydroxide (0.12 g) was added portion-wise sodium borohydride (3.04 g). The resulting mixture was heated under reflux for 2 hours. After cooling the solution was acidified with concentrated hydrochloric acid and the precipitate filtered off, washed with water and dried giving the title compound as a white solid, mp 235°.

EXAMPLE 41

Ethyl 5-fluoro-6,7,8,9-tetrahydro-4-oxo-10-propyl-4H-naphtho[2,3-b]pyran-2-carboxylate A solution of ethyl 5-chloro-6,7,8,9-tetrahydro-4-oxo-10-propyl-4H-naphtho[2,3-b]pyran-2-carboxylate (9 g) and desiccated potassium fluoride (2.32 g) in DMF (50 ml) was heated at 160° for 3.5 hours. After cooling, the reaction mixture was poured into water (250 ml) and the precipitate filtered off, washed with water and dried. Recrystallisation from cyclohexane gave the title compound as a pale-yellow solid, mp 126°–9°.

EXAMPLE 42

Ethyl 6,7,8,9-tetrahydro-4-oxo-10-(2-styryl)-4H-naphtho[2,3-b]pyran-2-carboxylate N-Butyl lithium (0.23 g) was added to a stirred suspension of benzyl triphenyl phosphonium chloride (1.34 g) in dry ether (75 mls) under nitrogen. After 25 minutes the product compound of Example 29(b) (1 g), suspended in dry ether (50 mls) was added. The reaction was allowed to stir for 65 hours and then poured into water (250 mls). The resulting mixture was extracted into methylene chloride (3×100 mls), which was then dried and evaporated to give a yellow solid (2.15 g). Chromatography on a silica column with ether as eluant produced the title compound as a crystalline yellow solid (1.25 g, 100%) mp 168°–169°. The ester may be hydrolysed to the free acid.

EXAMPLE 43

Ethyl 6,7,8,9-tetrahydro-4-oxo-10-(2-phenylethyl)-4H-benzo[2,3-b]pyran-2-carboxylate The product of Example 42 (0.6 g) in ethanol (150 mls) was hydrogenated over a 5% Pd/C catalyst (0.2 g) at atmospheric pressure. When the theoretical amount of hydrogen had been absorbed the catalyst was removed and the solvent evaporated to afford the title compound as a yellow solid (0.6 g, 100%) mp 156°–158°. The ester may be hydrolysed to the free acid.

EXAMPLE 44

5-Methoxy-4-oxo-10-propyl-4H-naphtho[2,3-b]pyran-2-carboxylic acid (a) Ethyl 5-methoxy-4-oxo-10-propyl-4H-naphtho[2,3-b]pyran-2-carboxylate The product of Example 28(a) (4.5 g) and potassium carbonate (2.0 g) were stirred together in dimethylformamide (150 ml), containing methyl iodide (6 ml), at room temperature for 24 hours. Further quantities of methyl iodide were added in portions of 2 ml, over the next 10 hours, until the total volume of the reagent used was 20 ml. Finally the mixture was heated on a steam bath for 1 hour, then cooled and poured into water. The resulting mixture was extracted into ethyl acetate and the organic layer was dried ($MgSO_4$) and evaporated, in vacuo, to yield the title ester (4.0 g) as a red oil.

(b) 5-Methoxy-4-oxo-10-propyl-4H-naphtho[2,3-b]pyran-2-carboxylic acid

The ester from step (a) (4.0 g) was hydrolysed to the corresponding acid (3.5 g) mp 245°–247°, using the method of Example 5(b).

(c) Sodium 5-methoxy-4-oxo-10-propyl-4H-naphtho[2,3-b]dipyran-2-carboxylate

The product of step (b) (3.4 g) was converted into its sodium salt (3.3 g) by the method of Example 4(d).

EXAMPLE 45

7,8-Dihydro-6-methyl-4-oxo-4H,6H-benzo[1,2-b,5,4-b']dipyran-2-carboxylic acid (a) 2,3-Dihydro-4-hydroxy-7-methoxy-4-methyl-4H-1-benzopyran Methyl iodide (145 g; 64.2 ml) in dry ether (50 ml) was added dropwise with stirring to magnesium turnings (22 g) in dry ether (730 ml). After the initial reaction had ceased the reaction mixture was refluxed for 1 hour, cooled and 2,3-dihydro-7-methoxy-4-oxo-4H-1-benzopyran, (77.9 g) in dry ether (440 ml) was added dropwise with stirring. After addition the reaction mixture was refluxed for 1 hour, cooled and the complex was decomposed by the addition of ammonium chloride solution. The ethereal layer was separated, washed with water and dried. Evaporation of the solvent left 76 g of the title compound as an oil (89%). MS and NMR analysis were correct for the required compound.

(b) 7-Methoxy-4-methyl-2H-1-benzopyran

The carbinol of step (a) (73.3 g) was stirred with phosphorus oxychloride (19.3 g; 11.6 ml) in dry pyridine (380 ml) for 20 hours under nitrogen. The reaction mixture was poured into water, extracted with ether and the ethereal extracts were washed with dilute acid, then sodium bicarbonate solution, then water and dried. Evaporation of the solvent left 58 g of residue (87.2%). MS evidence was correct for the required compound. NMR suggested that the product was in fact a mixture of isomeric alkenes.

(c) 2,3-Dihydro-7-methoxy-4-methyl-4H-1-benzopyran

The alkene mixture of step (b) (29 g) was dissolved in ethanol (300 ml) and hydrogenated in the presence of 5% palladium on charcoal (1.0 g) at 45 psi; until hydrogen uptake had ceased. The catalyst was filtered off through a supercel filter aid and the filtrate was evaporated to give the desired compound 29.2 g (99.4%). NMR and MS analysis were correct for the required compound.

(d) 6-Acetyl-2,3,-dihydro-7-methoxy-4-methyl-4H-1-benzopyran

The methyl ether of step (c) (58.0 g) was dissolved in dry benzene (1 l) and glacial acetic acid (22.3 ml) was added. Boron trifluoride gas was bubbled through the reaction mixture for 1 hour and then stirring was continued overnight. The reaction mixture was poured into water, the organic layer was separated and the aqueous phase was extracted with more ether. The organic extracts were washed with sodium bicarbonate solution, then water, and dried. Evaporation gave 67.8 g of the desired product (95%). MS and NMR analysis were correct for the required compound.

(e) 6-Acetyl-2,3,-dihydro-7-hydroxy-4-methyl-4H-1-benzopyran

The product of step (d) (57.4 g) in dry methylene chloride (500 ml) was treated with boron trichloride (61 g) in dry methylene chloride (150 ml) at −70° C. The cooling bath was removed and the reaction mixture was allowed to warm to room temperature during 1 hour. The reaction mixture was poured into water and the methylene chloride layer was separated, washed with water and dried. Evaporation of the solvent left 55.7 g of crude product; this was dissolved in ether and extracted several times with a sodium hydroxide solution. The basic extracts were acidified and the precipitated product extracted with ether, which was washed with water and dried. Evaporation of the solvent gave 35.4 g of product mp 91°–96°. A recrystallisation from ethanol gave the title compound, mp 101°–105°.

(i) Ethyl 7,8-dihydro-6-methyl-4-oxo-4H,6H-benzo[1,2-b,5,6-b']dipyran-2-carboxylate The product of step (c) (17.7 g) was treated with sodium (9.9 g) and diethyl oxalate (31.4 g) under the conditions of Example 1(d), to give the title compound (23.5 g), mp 114°–115°.

(g) 7,8-Dihydro-6-methyl-4-oxo-4H,6H-benzo[1,2-b:5,4-b']dipyran-2-carboxylic acid The ester of step (f) (21.5 g) was hydrolysed to the corresponding acid (13.9 g, mp 293° (decomp), by the method of Example 5(b).

(h) Sodium 7,8-dihydro-6-methyl-4-oxo-4H,6H-dibenzo[1,2-b:5.4-b']dipyran-2-carboxylate The acidic product from step (g) (5.0 g) was converted into its sodium salt (4.8 g), using the conditions of Example 4(d).

EXAMPLE 46

The following compounds may be made according to the processes described above:
(i) 6-Ethyl-6,7,8,9-tetrahydro-4-oxo-10-propyl-4H-naphtho[2,3-b]pyran-2-carboxylic acid.
(ii) 6,7,8,9-Tetrahydro-7-methyl-4-oxo-10-propyl-4H-naphtho[2,3-b]pyran-2-carboxylic acid.
(iii) 6,7,8,9-Tetrahydro-4-oxo-3,10-dipropyl-4H-naphtho[2,3-b]pyran-2-carboxylic acid.
(iv) 7,8-Dihydro-6-methyl-4-oxo-10-propyl-4H,6H-benzo[1,2-b:5,4-b']dipyran-2-carboxylic acid.
(v) 6-Ethyl-6,7,8,9-tetrahydro-4-oxo-4H-naphtho[2,3-b]pyran-2-carboxylic acid.
(vi) 6,7,8,9-Tetrahydro-7-methyl-4-oxo-4H-naphtho[2,3-b]pyran-2-carboxylic acid.
(vii) 7,8-Dihydro-4-oxo-10-(2-styryl)-4H,6H-benzo[1,2-b 5,4-b']dipyran-2-carboxylic acid.
(viii) 7,8-Dihydro-4-oxo-10-(2-phenylethyl)-4H,6H-benzo[1,2-b:5,4-b']dipyran-2-carboxylic acid.
(ix) 10-(2-Chloropropyl)-6,7,8,9-tetrahydro-4-oxo-4H-naphtho[2,3-b]pyran-2-carboxylic acid.
(x) 10-(Cyclohexylmethyl)-6,7,8,9-tetrahydro-4-oxo-4H-naphtho[2,3-b]pyran-2-carboxylic acid.
(xi) 10-(n-Hexyl)-6,7,8,9-tetrahydro-4-oxo-4H-naphtho[2,3-b]pyran-2-carboxylic acid.
(xii) 6,7,8,9-Tetrahydro-4-oxo-10-(3-oxobutyl)-4H-naphtho[2,3-b]pyran-2-carboxylic acid.
(xiii) 10-(Hex-1-enyl)-6,7,8,9-tetrahydro-4-oxo-4H-naphtho[2,3-b]pyran-2-carboxylic acid.
(xiv) 10-(2-Cyclopentylethyl)-6,7,8,9-tetrahydro-4-oxo-4H-naphtho[2,3-b]pyran-2-carboxylic acid.
(xv) 10-(Cyclohexylmethyl)-7,8-dihydro-4-oxo-4H,6H-benzo[1,2-b:5,4-b']dipyran-2-carboxylic acid.
(xvi) 6,7,8,9-Tetrahydro-5-methyl-4-oxo-10-propyl-4H-naphtho[2,3-b]pyran-2-carboxylic acid.

EXAMPLE A

| Tablet formulation | mg/tablet | % by weight |
|---|---|---|
| 1. Compound of formula I, e.g. of Example 8(a) | 15 | 9.3 |
| 2. Mannitol BP | 90 | 55.5 |
| 3. Maize Starch BP | 15 | 9.3 |
| 4. Microcrystalline cellulose BPC | 30 | 18.5 |
| 5. Polyvinylpyrrolidone | 10 | 6.2 |
| 6. Magnesium stearate BP | 2 | 1.2 |

Items 1-4 are dry mixed, then moistened with an aqueous solution of item 5, passed through an 8 mesh screen and dried for 3 hours at 60° C. The dry product is passed through a 16 mesh screen and blended with item 6. The final mixture is compressed to a Monsanto hardness of 3 to 5 kg.

| Capsule formulation | mg/tablet | % by weight |
|---|---|---|
| 1. Compound of formula I, e.g. of Example 1(f) | 15 | 9.6 |
| 2. Lactose BP | 90 | 57.3 |
| 3. Maize starch BP | 50 | 31.8 |
| 4. Magnesium stearate BP | 2 | 1.3 |

All of the ingredients are blended and filled into empty hard gelatin capsule shells on a capsule filling machine.

We claim:

1. A compound of the formula

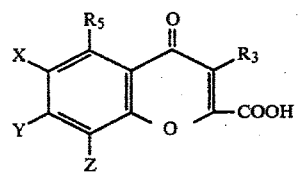

in which
R$_3$ represents hydrogen, or alkyl C 1 to 6,
R$_5$ represents hydrogen, hydroxy, alkoxy C 1 to 6, alkanoyloxy C 2 to 6, alkenyloxy C 2 to 6, nitro, —NR$_1$R$_2$, halogen, alkyl C 1 to 6, hydroxy-alkyl C 1 to 6, or hydroxyalkoxy C 1 to 6;
an adjacent pair of X, Y and Z form an —O(CH$_2$)$_3$— chain which is unsubstituted or substituted by one or two C 1 to 6 alkyl groups, and the remaining substituent X or Z represents alkenyl C 2 to 6 unsubstituted or substituted by phenyl; halogen; cyclohexylmethyl, cyclopentylmethyl, or cyclopentylethyl; or alkyl C 1 to 9 unsubstituted or substituted by one or more of the groups hydroxy, halogen, carbonyl oxygen, phenyl, or alkoxy C 1 to 6;
or, when an adjacent pair of X, Y and Z form said chain substituted by one or two C 1 to 6 alkyl groups the remaining substituent X or Z is hydrogen, and
R$_1$ and R$_2$, which may be the same or different, are each hydrogen or alkyl C 1 to 6,
or a pharmaceutically acceptable salt, ester or amide thereof.

2. A compound in accordance with claim 1 wherein R$_3$ is hydrogen or straight or branched alkyl C 1 to 4,
R$_5$ is hydrogen; hydroxy; alkoxy C 1 to 3; acetoxy; allyloxy; nitro; amino; mono- or di-alkyl C 1 to 4 amino; chlorine or fluorine; straight or branched alkyl C 1 to 4; hydroxy-alkyl C 1 to 4; or hydroxyalkoxy C 1 to 4,
and, in said chain formed by an adjacent pair of X, Y and Z, the remaining substituent X or Z represents hydrogen; straight or branched alkyl C 1 to 8; cyclohexylmethyl, cyclopentylmethyl, or cyclopentylethyl; allyl or hex-1-enyl; bromine or chlorine; mono or di-hydroxyalkyl C 1 to 4; chloro-alkyl C 1 to 4; chloro-hydroxyalkyl C 1 to 4; oxo-substituted alkyl C 1 to 4; phenyl-alkyl in which the alkyl contains from 1 to 3 carbon atoms; styryl; or alkoxy C 1 to 4—alkyl C 1 to 4.

3. A compound according to claim 2, wherein R$_3$ is hydrogen or methyl;
R$_5$ is hydrogen; hydroxy; methoxy; propoxy, acetoxy; allyloxy; nitro; amino; dimethylamino; monoethylamino; chlorine; fluorine; methyl; hydroxymethyl; or 2-hydroxy-propoxy,
and said remaining substituent X or Z represents hydrogen; ethyl; n-propyl; n-hexyl; cyclohexylmethyl; cyclopentylmethyl; hex-1-enyl; allyl; bromine; chlorine; 2-hydroxy-propyl; chloro-propyl; chloro-hydroxy-propyl; formyl; propionyl; 3-oxobutyl; benzyl; phenyl-ethyl; styryl; or ethoxymethyl.

4. A compound according to claim 1 and selected from:
7,8-dihydro-4-oxo-10-propyl-4H,6H-benzo[1,2-b: 5,4-b']dipyran-2-carboxylic acid,
8,9-dihydro-5-methoxy-8,8-dimethyl-4-oxo-4H,10H-benzo[1,2-b: 3,4-b']dipyran-2-carboxylic acid,
7,8-dihydro-6-methyl-4-oxo-4H,6H-benzo[1,2-b, 5,4,-b']dipyran-2-carboxylic acid,
7,8-dihydro-6-methyl-4-oxo-10-propyl-4H,6H-benzo[1,2-5,4-b']dipyran-2-carboxylic acid,
7,8-dihydro-4-oxo-10-(2-styryl)-4H,6H-benzo[1,2-b: 5,4-b']dipyran-2-carboxylic acid,
7,8-dihydro-4-oxo-10-(2-phenylethyl)-4H,6H-benzo[1,2-b: 5,4-b']dipyran-2-carboxylic acid,
10-(cyclohexylmethyl)-7,8-dihydro-4-oxo-4H,6H-benzo[1,2-b: 5,4-b']dipyran-2-carboxylic acid.

5. A compound according to claim 1, wherein X and Y together form a chain.

6. A compound according to claim 1, wherein R$_3$ is hydrogen, R$_5$ is hydrogen, hydroxy, amino, mono- or di-alkyl amino, fluorine or alkoxy and the substituent X or Z which does not form part of a chain is propyl.

7. A compound according to claim 1, wherein R$_5$ is hydrogen, hydroxy, —NH$_2$, —N(CH$_3$)$_2$, —NHC$_2$H$_5$, fluorine, chlorine or methoxy.

8. A compound according to claim 1 in the form of the ethyl ester thereof.

9. A compound according to claim 1 in a form having a mass median diameter of from 0.01 to 10 microns.

* * * * *

UNITED STATES PATENT OFFICE
CERTIFICATE OF CORRECTION

Patent No. 4,238,606     Dated  December 9, 1980

Inventor(s) Roger C. Brown, Richard Hazard, and John Mann

It is certified that error appears in the above-identified patent and that said Letters Patent are hereby corrected as shown below:

Abstract, line 5, "R_S" should be --R_5--; Column 2, line 49, "COOM" should be --COOH--; Column 6, line 54, "OOCH" should be --COOH--; Column 7, line 57, "(c)" should be --(e)--; Column 9, line 42, "PD/C" should be --Pd/C--; Column 15, line 34, "cyclopentylethyl" should be --cyclohexylmethyl--; Column 16, line 40, "801" should be --80%--; Column 16, line 40, "501" should be --50%--; Column 16, line 47, "manaitol" should be --mannitol--; Column 17, line 6, "Tetrahydro-1" should be --Tetrahydro-4--; Column 17, line 7, "h]" should be --b]--; Column 17, line 42, "ono" should be --oxo--; Column 17, line 43, "pyra" should be --pyran--; Column 17, line 46, "(150 g)" should be --(180 g)--; Column 17, line 61, "(201 g)" should be --(202 g)--; Column 18, line 20, "(0.2 g)" should be --(0.24 g)--; Column 18, line 30, "2.8 g" should be --2.5 g--; Column 18, line 57, "alkyl" should be --allyl--; Column 19, line 9, "pyra" should be --pyran--; Column 19, line 68, "30°" should be --80°--; Column 20, line 21, "3.5 g" should be --8.5 g--; Column 21, line 7, "1(c)" should be --1(e)--; Column 22, line 25, "133°" should be --138°--; Column 22, line 43, "(31.0 g)" should be --(34.0 g)--; Column 22, line 51, "(80 ml)" should be --(90 ml)--; Column 23, line 6, "(0.591 g)" should be --(0.594 g)--; Column 23, line 38, "naphtho8" should be --naphtho[--; Column 23, line 45, "245°-50" should be --245°-8°--; Column 24, line 51, "(310 mg)" should be --(340 mg)--; Column 24, line 56, "by hydrolysis" should be --hydrolysis--; Column 25, line 66, "(2.40 g)" should be --(2.49 g)--; Column 26, line 28, "41" should be --4--; Column 27, line 9, "coolig" should be --cooling--; Column 28, line 59, "NR" should be --NMR--; Column 29, line 8, "NR" should be --NMR--; Column 29, line 45, "[1,2-bis," should be --1,2-b:5,--; Column 29, line 54, "S-allyl" should be --8-allyl--; Column 29, line 65, "(19 g)" should be --(10 g)--;

UNITED STATES PATENT AND TRADEMARK OFFICE
CERTIFICATE OF CORRECTION

PATENT NO. : 4,238,606

DATED : December 9, 1980

INVENTOR(S) : Roger C. Brown et al.

It is certified that error appears in the above—identified patent and that said Letters Patent is hereby corrected as shown below:

Column 30, line 16, "(8.6 g)" should be --(8.0 g)--; Column 30, line 24, "(c)" should be --(e)--; Column 30, line 24, "(4.61 g)" should be --(4.64 g)--; Column 31, line 14, "ethoxy" should be --methoxy--; Column 32, line 40, "1-hydroxy" should be --5-hydroxy--; Column 33, line 52, "ethoxyethyl" should be --ethoxymethyl--; Column 35, line 17, "(73%)" should be --(78%)--; Column 38, lines 7-8, "benzo" should be --naphtho--; Column 38, line 45, "dipyran" should be --pyran--; Column 38, line 61, "1" should be --1/2--; Column 39, line 58, "35.4" should be --36.4--; Column 39, line 60, "101°" should be --104°--; Column 39, line 61, "(i)" should be --(f)--; Column 39, line 63, "5,6" should be --5,4--; Column 39, line 65, "(c)" should be --(e)--; Column 40, line 10, "dibenzo" should be --benzo--.

Signed and Sealed this

Second Day of June 1981

[SEAL]

Attest:

RENE D. TEGTMEYER

Attesting Officer

Acting Commissioner of Patents and Trademarks